(12) United States Patent
Wallace et al.

(10) Patent No.: US 10,980,628 B2
(45) Date of Patent: Apr. 20, 2021

(54) JOINT STABILISATION

(71) Applicants: XIROS LIMITED, Leeds (GB); William Angus Wallace, Nottingham (GB); Matthew John Ravenscroft, Mere (GB)

(72) Inventors: William Angus Wallace, Nottingham (GB); Matthew John Ravenscroft, Mere (GB); Benjamin John Young, Leeds (GB); David John Beevers, Leeds (GB); Bahaa Botros Seedhom, Leeds (GB)

(73) Assignee: XIROS LIMITED, Leeds (GB)

( * ) Notice: Subject to any disclaimer, the term of this patent is extended or adjusted under 35 U.S.C. 154(b) by 296 days.

(21) Appl. No.: 15/745,904

(22) PCT Filed: Jul. 20, 2016

(86) PCT No.: PCT/GB2016/052202
§ 371 (c)(1),
(2) Date: Jun. 25, 2018

(87) PCT Pub. No.: WO2017/013431
PCT Pub. Date: Jan. 26, 2017

(65) Prior Publication Data
US 2018/0296318 A1 Oct. 18, 2018

(30) Foreign Application Priority Data
Jul. 20, 2015 (GB) ...................................... 1512682

(51) Int. Cl.
*A61F 2/08* (2006.01)
*A61B 17/04* (2006.01)

(52) U.S. Cl.
CPC ............ *A61F 2/0811* (2013.01); *A61B 17/04* (2013.01); *A61F 2/08* (2013.01); *A61F 2002/087* (2013.01);
(Continued)

(58) Field of Classification Search
CPC .. A61F 2/08; A61F 2/0811; A61F 2002/0852; A61F 2002/0858;
(Continued)

(56) References Cited

U.S. PATENT DOCUMENTS 5,699,657 A 12/1997 Paulson
6,296,659 B1 * 10/2001 Foerster ............. A61B 17/0469
606/224

(Continued)

FOREIGN PATENT DOCUMENTS

GB        2502959 A    12/2013

OTHER PUBLICATIONS

International Search Report and Written Opinion dated Oct. 20, 2016 for PCT/GB2016/052202.
(Continued)

*Primary Examiner* — Brian A Dukert
(74) *Attorney, Agent, or Firm* — Stoel Rives LLP

(57) ABSTRACT

There is disclosed a synthetic joint stabilisation device (10) and associated assembly, the device having a particular use in a method of stabilising a dislocated acromioclavicular joint. The joint stabilisation device (10) comprises a first elongate portion (22) forming a first free end (24); a second elongate portion (26) forming a second free end (28) which is opposite the first free end; and an integral eye (30) provided at a location which is between the first and second free ends, the eye serving for securing the device to a bone (19) of a patient. The device (10) is at least partly tubular so as to define an internal cavity (32), said part, of the device (Continued)

being of a woven material. One of the first and second elongate portions (22, 26) extends into the internal cavity (32) through a wall (34) of the other one of the first and second elongate portions at a first location (36) along a length of said other portion, and then extends out of the internal cavity at a second location (38) which is spaced along a length of said other portion from the first location, to thereby form a loop (40) which defines the eye.

22 Claims, 19 Drawing Sheets

(52) U.S. Cl.
CPC .................. *A61F 2002/0852* (2013.01); *A61F 2002/0858* (2013.01); *A61F 2002/0882* (2013.01); *A61F 2250/001* (2013.01); *A61F 2250/0087* (2013.01)

(58) Field of Classification Search
CPC ...... A61F 2002/0882; A61F 2250/0085; A61F 2250/0087; A61F 2250/0089; A61B 17/04; A61B 17/0401; A61B 17/06166; A61B 2017/06185; A61B 2017/06057
See application file for complete search history.

(56) References Cited

U.S. PATENT DOCUMENTS

| | | |
|---|---|---|
| 6,355,066 B1 | 3/2002 | Kim |
| 2008/0255613 A1 | 10/2008 | Kaiser et al. |
| 2010/0292792 A1 | 11/2010 | Stone et al. |
| 2011/0295284 A1 | 12/2011 | Purdue et al. |
| 2015/0141995 A1* | 5/2015 | Norton ................. A61B 17/823 606/74 |

OTHER PUBLICATIONS

"LockDown Acromioclavicular (AC) Device", LockDown Surgical Inc., http://lockdownsurgical.com/wp-content/uploads/2014/03/lockdown-US-2PP-A5_UK_revised.pdf.
Neoligaments, "AcromioTape System", Surgical Technique Manual, https://www.neoligaments.com/wp-content/uploads/2015/09/Lab-090-AcromioTape-System-Stabilization-of-the-Dislocated-Acromioclavicular-Joint-with-Associated-Disruption-of-the-Coracoclavicular-Ligaments-Surgical-Technique-Manual.pdf, 2015.

* cited by examiner

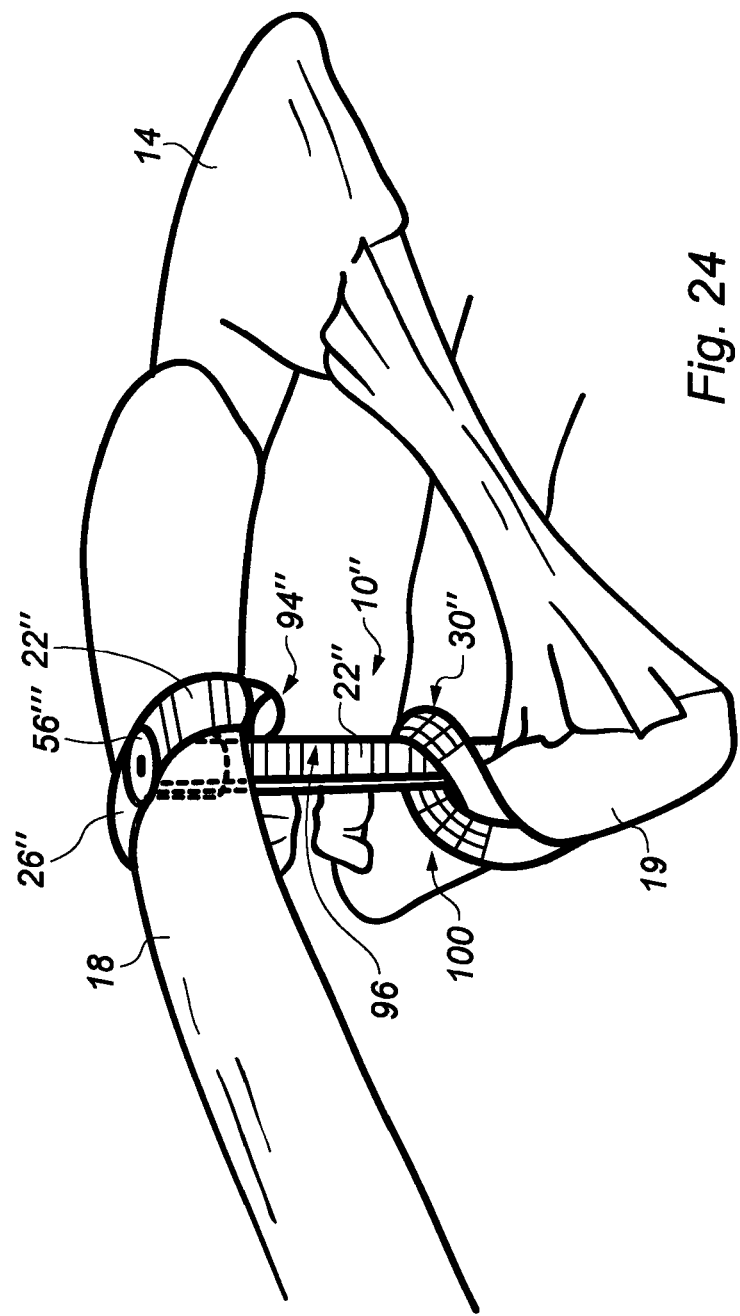

JOINT STABILISATION

RELATED APPLICATIONS

This application is the U.S. National Stage filing under 35 U.S.C. § 371 of International Patent Application No. PCT/GB2016/052202, filed on Jul. 20, 2016 and titled JOINT STABILISATION, which claims the benefit of Great Britain Patent Application No. 1512682.4, filed on Jul. 20, 2015 and titled JOINT STABILISATION, each of which is incorporated herein by reference in their entirety.

The present invention relates to a synthetic joint stabilisation device. In particular, but not exclusively, the present invention relates to a synthetic joint stabilisation device having a use in a method of stabilising a dislocated acromioclavicular joint. The present invention also relates to a synthetic joint stabilisation assembly, and to a method of stabilising a dislocated joint.

The acromioclavicular joint ('ACJ') is a joint at the top of the shoulder. Specifically, the ACJ is the junction between the acromion, which is part of the scapula, and the clavicle. Numerous ligaments exist in the ACJ, including: the coracoclavicular ligament ('CC ligament'), which extends between the coracoid process of the scapula and the clavicle; the acromioclavicular ligament ('AC ligament'), which extends between the acromion and the clavicle; and the coracoacromial ligament ('CA ligament'), which extends between the coracoid process and the acromion.

An ACJ dislocation is where the clavicle becomes separated from the acromion, due to damage to the ligaments in the ACJ, and particularly damage to the CC ligament and/or the AC ligament. ACJ dislocations are graded from I to VI, according to the degree of separation of the clavicle from the acromion (with weight applied to the associated arm). A stage I dislocation involves a slight displacement of the joint, and a badly stretched or partially torn AC ligament. Complete rupture of the CC ligaments, with dislocation of the joint, is usually classified as a stage II, III or IV acromioclavicular injury, depending upon the location of the clavicle.

ACJ dislocation is a common injury in many impact-based sports, such as judo, rugby football and American football. It is also prevalent in sports such as horse riding, skiing, snowboarding and mountain biking, where injury typically occurs due to a fall. ACJ dislocation occurring during a fall typically involves an impact on the tip of the shoulder, or an outstretched hand transferring an impact load to the ACJ.

An ACJ dislocation can result in the powered movement of the shoulder being permanently diminished. In young, active patients, this imposes serious lifestyle limitations, not only in sports and recreation, but also in employment, because it precludes many manual labour-based tasks. Accordingly, surgical techniques, synthetic joint stabilisation devices, and synthetic joint stabilisation assemblies have been developed which seek to stabilise and so restore function to dislocated ACJs, and in particular to repair damaged ligaments (especially torn CC and AC ligaments), and to reduce the clavicle relative to the acromion.

One prior synthetic joint stabilisation assembly having a use in ACJ stabilisation is the LockDown™ AC Device, which is commercially available from LockDown Surgical, Inc. in the USA. The LockDown™ AC Device is a synthetic joint stabilisation device having a fixed length, with loops provided at opposed ends of the device. The device is implanted by passing it around the coracoid process, directing one end of the device through one of the loops to secure the device to the coracoid process, and then passing that end of the device around the clavicle and anchoring it to the clavicle using a fixation screw which clamps the loop at that end of the device to the bone.

The LockDown™ AC Device suffers from the significant disadvantage that the length of the synthetic device is fixed, which means that a surgeon does not have an ability to vary the length of the device to suit the ACJ of a particular patient. Rather, it is necessary to select a device having a fixed length, suited to the patient. This requires that a large range of devices of different lengths be provided. In addition, the implantation procedure requires an initial step of performing measurements of the ACJ, before the device can be implanted. This requires additional equipment, takes time, and adds an extra level of complexity to the implantation procedure, all of which are undesirable.

The present invention seeks to provide an improved surgical method, synthetic joint stabilisation device, and synthetic joint stabilisation assembly having a use particularly in ACJ stabilisation. The method, device and assembly may, however, have uses in other surgical procedures and so in the stabilisation of other joints.

According to a first aspect of the present invention, there is provided a synthetic joint stabilisation device comprising:
  a first elongate portion forming a first free end;
  a second elongate portion forming a second free end which is opposite the first free end; and
  an integral eye provided at a location which is between the first and second free ends, the eye serving for securing the device to a bone of a patient;
  in which the device is at least partly tubular so as to define an internal cavity, said part of the device being of a textile (preferably woven) material;
  and in which one of the first and second elongate portions extends into the internal cavity through a wall of the other one of the first and second elongate portions at a first location along a length of said other portion, and then extends out of the internal cavity at a second location which is spaced along a length of said other portion from the first location, to thereby form a loop which defines the eye.

Providing a synthetic joint stabilisation device which is at least partly tubular, said part of the device being of a woven material, provides the advantage that warp and weft yarns (or filaments) of the woven material can easily be separated so that said one of the first and second elongate portions can be passed into and out of the internal cavity. This facilitates formation of the loop. In addition, it is easy to adjust a dimension of the loop during manufacture of the device, because the woven structure of the material facilitates sliding movement between the elongate portions.

The elongate portions may be secured against movement relative to one another, to prevent the other one of the elongate portions from moving within the internal cavity, thereby fixing a dimension of the loop. This may be achieved by stitching, suturing, whipping or fusing the elongate portions together, or by a combination of two or more such techniques.

It may be desirable to provide a device in which movement of the elongate portions relative to one another is possible (in particular sliding movement of said one of the elongate portions within the internal cavity), to facilitate adjustment of a dimension of the loop. Adjustment of the dimension of the loop may be desirable during implantation of the device within a body of a patient. Adjustment may be achieved by translating the one of the elongate portions extending into and out of the internal cavity relative to the other one of the elongate portions.

The device may comprise at least one indicator, which may be associated with a part of the device, the at least one indicator facilitating identification of said part of the device during use. In particular, the at least one indicator may facilitate identification of said part of the device during implantation of the device within a body of a patient. This may be particularly beneficial in circumstances where the implantation procedure is carried out arthroscopically.

The device may comprise a plurality of indicators, each indicator associated with a different part of the device, facilitating identification of the different parts of the device associated with the respective indicator.

The at least one indicator may be a visual indicator and may have a visual characteristic. The at least one indicator may comprise a part of the device which is coloured, and/or of a colour which is different from at least one other part or parts of the device.

At least one of the first and second elongate portions may comprise at least one indicator. The at least one indicator may therefore facilitate identification of said elongate portion, during use. This may provide an indication of the one of the elongate portions extending into and out of the internal cavity. This may be useful, because adjustment of the dimension of the loop may be achieved by translating said elongate portion relative to the other elongate portion, the indicator providing an indication of which one of the portions to translate.

The first and the second elongate portions may each comprise at least one indicator. In this situation, the at least one indicator associated with the first elongate portion may be a different indicator from the at least one indicator associated with the second elongate portion. The respective indicators of the elongate portions may have different characteristics, which may be visual characteristics. The at least one indicator of the first elongate portion may differ from the at least one indicator of the second elongate portion visually, and may for example be of different colours.

The device may comprise at least one first indicator having a first indicator characteristic, and at least one second indicator having a second characteristic which is different from the first characteristic. This may facilitate identification of different parts of the device associated with each of the first and second indicators. The characteristic may be a visual characteristic. The device may comprise an indicator associated with the integral eye, facilitating identification of the eye. The device may comprise an indicator associated with at least one of the free ends, facilitating identification of said end.

The device may be entirely of a textile, optionally woven material.

The device may be tubular over a majority of its length, and optionally over an entirety of its length. The device may comprise one or more tubular sections, a remainder or other parts of the device being non-tubular. At least a mid-section of the device may be tubular, so that the eye can be formed at or in the mid-section.

The device may be closed at the first and/or second ends.

The first elongate portion may extend from an apex of the eye to the first free end. The second elongate portion may extend from an apex of the eye to the second free end.

The eye may be an integral eye in that a material forming the first and second elongate portions may also form the eye. The eye may be integral in that the first and second elongate portions and the eye may be formed from a single elongate structure. The eye may comprise part of the first elongate portion and part of the second elongate portion. The eye may comprise the parts of the first and second elongate portions which extend from an apex of the eye to the first location.

The synthetic joint stabilisation device may have a use in the stabilisation of a dislocated acromioclavicular joint (ACJ). The device may be a synthetic coracoclavicular (CC) repair device, and so may be used to perform at least part of the function of a damaged CC ligament. The device may be a synthetic CC and acromioclavicular (AC) repair device, and so may be used to perform at least part of the function of damaged CC and AC ligaments. The device may be adapted to repair sterno-clavicular ligaments. It will be understood that the device may effectively act on behalf of a damaged ligament, may appose a damaged ligament, and/or may maintain joint bones at one or more ligament attachment points, thereby replacing its function.

The joint stabilisation device may have other uses than in the stabilisation of a dislocated ACJ. The stabilisation device may be used to perform at least part of the function of other damaged tissue, including but not restricted to tendons. For example, the stabilisation device/assembly and method may have a use in stabilisation of an elbow joint, and so of the collateral ligaments at the elbow, as well as repairs of distal biceps tendon avulsion.

According to a second aspect of the present invention, there is provided a synthetic joint stabilisation assembly comprising:
  a synthetic joint stabilisation device according to the first aspect of the present invention; and
  at least one fixation device, for securing at least one of the first and second elongate portions within a tunnel in a bone.

Further features of the synthetic joint stabilisation device may be derived from the text set out above relating to the first aspect of the invention. Further features of the at least one fixation device may be derived from the text set out elsewhere in this document, particularly from the text set out below relating to the third aspect of the invention.

According to a third aspect of the present invention, there is provided a synthetic acromioclavicular joint (ACJ) stabilisation assembly comprising:
  a synthetic joint stabilisation device having:
    a first elongate portion forming a first free end;
    a second elongate portion forming a second free end which is opposite the first free end; and
    an integral eye provided at a location which is between the first and second free ends;
  and at least one fixation device;
  in which the joint stabilisation device is adapted to be secured to a coracoid process of the ACJ by passing the device around the coracoid process and directing the first and second free ends through the eye, to form a loop extending around the coracoid process;
  and in which the joint stabilisation device is adapted to be secured to a clavicle of the ACJ using the at least one fixation device, the fixation device adapted to be located in a tunnel in the clavicle and to engage at least one of the elongate portions at a location which is spaced along a length of the elongate portion from its free end.

The synthetic ACJ stabilisation assembly of the present invention provides the advantage that a length of the synthetic device is not fixed prior to implantation. A surgeon can select a desired length of the device by securing it relative to a bone (in particular the clavicle) at a location or locations which are spaced along a length of the device from the first and/or second free ends. The synthetic joint stabilisation device may therefore be provided of a length which is greater than the likely maximum length required for an ACJ stabilisation procedure employing the device, with the surgeon setting the final length during the implantation procedure. This is in contrast to prior assemblies of the type described above, where the length of the synthetic device is fixed prior to the surgical procedure.

The device may be at least partly tubular so as to define an internal cavity, said part of the device (and optionally the entire device) being of a textile, preferably a woven material. One of the first and second elongate portions may extend into the internal cavity through a wall of the other one of the first and second elongate portions at a first location along a length of said other portion, and may then extend out of the internal cavity at a second location which is spaced along a length of said other portion from the first location, to thereby form a loop which defines the eye.

The elongate portions may be secured against movement relative to one another, to prevent said one of the elongate portions from moving within the internal cavity, thereby fixing a dimension of the loop. This may be achieved by stitching, suturing, whipping or fusing the elongate portions together, or by a combination of two or more such techniques. However, it may be desirable to provide a device in which movement of the elongate portions relative to one another remains possible, to facilitate adjustment of a dimension of the loop.

The joint stabilisation device may be entirely of a textile material, in particular a woven material.

The joint stabilisation device may be tubular over a majority of its length, and optionally over an entirety of its length. The device may comprise one or more tubular sections, a remainder or other parts of the device being non-tubular. At least a mid-section of the device may be tubular, so that the eye can be formed at or in the mid-section.

The joint stabilisation device may be closed at the first and/or second ends.

The first elongate portion may extend from an apex of the eye to the first free end. The second elongate portion may extend from an apex of the eye to the second free end.

The eye may be an integral eye in that a material forming the first and second elongate portions may also form the eye. The eye may be integral in that the first and second elongate portions and the eye may be formed from a single elongate structure. The eye may comprise part of the first elongate portion and part of the second elongate portion. The eye may comprise the parts of the first and second elongate portions which extend from an apex of the eye to the first location.

The assembly may comprise a first fixation device adapted to be located in a first tunnel in the clavicle, and to engage the first elongate portion of the joint stabilisation device at a location which is spaced along a length of said portion from its free end; and a second fixation device adapted to be located in a second tunnel in the clavicle, and to engage the second elongate portion of the joint stabilisation device at a location which is spaced along length of said portion from its free end. It will therefore by understood that each elongate portion of the joint stabilisation device may be located in separate tunnels in the clavicle, and secured using respective fixation devices.

A single fixation device may be provided which is adapted to be located in a tunnel in the clavicle, and to engage the first and second elongate portions of the joint stabilisation device at locations which are spaced along lengths of said portions from their free ends. It will therefore by understood that both elongate portions of the device may be located in a common tunnel in the clavicle, and secured using a common fixation device.

The at least one fixation device may comprise a locating part adapted to be located in the tunnel, and an abutment part. The abutment part may be adapted to abut an outer surface of the clavicle. The abutment part may be adapted to abut said elongate portion, which may assist in securing said elongate portion to the clavicle.

The at least one fixation device may be a plug, which may have an at least partly solid cross-section, the plug being adapted to clamp or trap said elongate portion between an outer surface of the plug and a wall of the tunnel, suitably via an interference fit with the bone tunnel. The plug may be at least partly tapered, and may have a tapered leading end. This may facilitate insertion of the fixation device into the bone tunnel, and/or may reduce a likelihood of damaging the stabilisation device during insertion of the fixation device. The plug may have a main plug portion, which may serve for clamping/trapping said elongate portion. The main plug portion may be generally cylindrical and may be of a substantially uniform diameter. The main portion may be substantially free from projections, and/or may be substantially smooth-sided.

The at least one fixation device may be a threaded device having an external thread which is adapted to engage a wall of the tunnel to secure the device within the tunnel, and to clamp or trap said elongate portion between an outer surface of the device and a wall of the tunnel.

The at least one fixation device may comprise a passageway extending through the device, for receiving said elongate portion. The fixation device may be a generally annular member, such as a collar. The fixation device may comprise a flange which is adapted to abut an outer surface of the clavicle to retain the device in the tunnel. The flange may define the abutment surface. The fixation device may engage an enlarged dimension section of said elongate portion to secure it relative to the clavicle, by abutment between the abutment part and the enlarged dimension section. The enlarged dimension section may be a knot formed in said elongate portion, and/or between the elongate portions.

The joint stabilisation device may be adapted to be secured to the coracoid process by passing it around an inferior surface of the coracoid process and then directing the free ends through the eye. The loop may extend around a perimeter of the coracoid process.

According to a fourth aspect of the present invention, there is provided a method of stabilising a dislocated acromioclavicular joint (ACJ), the method comprising the steps of:
  providing a synthetic joint stabilisation device having a first elongate portion forming a first free end, a second elongate portion forming a second free end which is opposite the first free end, and an integral eye provided at a location which is between the first and second free ends;
  passing the joint stabilisation device around a coracoid process of the ACJ;
  directing the first and second free ends of the device through the eye to form a loop extending around the coracoid process;
  applying tension to the device to shorten the loop, thereby securing the device to the coracoid process;
  directing the first free end of the device through a tunnel in the clavicle;
  directing the second free end of the device through a tunnel in the clavicle;

reducing the clavicle relative to the coracoid process;
applying tension to the first and second elongate portions of the device;
securing the first elongate portion of the joint stabilisation device to the clavicle using a fixation device inserted into a mouth of the tunnel in which the first elongate portion is located, the fixation device engaging the first elongate portion at a location which is spaced along the length of said portion from the first free end; and
securing the second elongate portion of the joint stabilisation device to the clavicle using a fixation device inserted into a mouth of the tunnel in which the second elongate portion is located, the fixation device engaging the second elongate portion at a location which is spaced along the length of said portion from the second free end.

The step of reducing the clavicle may comprise urging the clavicle towards the coracoid process. Reduction of the clavicle may be achieved at least in part by manipulating at least one of the elongate portions so to urge the clavicle towards the coracoid process.

The method may comprise: directing the first free end of the joint stabilisation device through a first tunnel in the clavicle; directing the second free end of the joint stabilisation device through a second tunnel in the clavicle; inserting a first fixation device into the first tunnel and securing the first elongate portion in the first tunnel using the first fixation device; and inserting a second fixation device into the second tunnel and securing the second elongate portion in the second tunnel using the second fixation device.

The method may comprise: directing the first and second free ends of the joint stabilisation device through a common tunnel in the clavicle; inserting the fixation device into the common tunnel, and securing both the first and second elongate portions in the common tunnel using the fixation device.

One of the first and second elongate portions may extend into an internal cavity of the stabilisation device through a wall of the other one of the first and second elongate portions at a first location along a length of said other portion, and may then extend out of the internal cavity at a second location which is spaced along a length of said other portion from the first location, to thereby form a loop which defines the eye.

The method may comprise adjusting a dimension of the eye. The adjustment may comprise reducing a dimension of the eye. Adjustment of the dimension may be achieved by translating the one of the elongate portions extending into and out of the internal cavity relative to the other one of the elongate portions. Adjustment may take place during implantation of the stabilisation device. Adjustment may take place following the step of directing the free ends of the device through the eye. Adjustment may take place following the step of directing the free ends through a tunnel in the clavicle.

The fixation device may clamp said elongate portion between an outer surface of the device and a wall of the tunnel.

The fixation device may be a threaded device having an external thread so that it engages a wall of the tunnel to secure the device within the tunnel, and to clamp said elongate portion between an outer surface of the device and a wall of the tunnel.

The method may comprise locating a fixation device within a tunnel in the clavicle, the device comprising a passageway extending through it, and directing said first and/or second free end of the joint stabilisation device through the passageway.

The method may comprise clamping said first and/or second elongate portion to an outer surface of the clavicle via a flange on the fixation device.

The method may comprise forming a knot on one or both of the elongate portions, the at least one fixation device engaging the knot to secure said elongate portion to the clavicle. The method may comprise tying the first and second elongate portions together at locations which are closer to their first and second ends than the location at which the elongate portions are engaged by the at least one fixation device. The or each knot may be superior to the clavicle. The method may comprise passing the free ends around the clavicle and then tying the elongate portions together via a knot which is located inferiorly relative to the clavicle.

The method may comprise the further step of directing the first and second free ends towards the acromion, and securing the first and second elongate portions relative to the acromion. Tension may be applied to sections of the elongate portions extending between the clavicle and the acromion prior to securement.

The method may comprise directing at least one of the first and second free ends of the joint stabilisation device through a tunnel in the acromion. At least one of the elongate portions may be secured within the tunnel using a further fixation device.

The method may comprise directing one of the first and second free ends through a tunnel in the acromion, and attaching the elongate portions to one another to thereby secure them relative to the acromion. A further fixation device may also be located in the tunnel to secure the elongate portion residing in the tunnel. The elongate portions may be secured by tying them together, and so by a knot. Said free end may be passed in an interior to superior direction through the tunnel, and the elongate portions secured together at a superior location. Said free end may be passed in a superior to inferior direction through the tunnel, and the elongate portions secured together at an inferior location.

The method may comprise directing both the first and second free ends of the joint stabilisation device through a tunnel in the acromion. The free ends may be passed in different directions through the tunnel. The elongate portions may be secured within the tunnel using a further fixation device.

The elongate portions may be severed at a location between the clavicle and the free ends, following securement.

Further features of the method of the fourth aspect of the invention may be derived from the text set out elsewhere in this document, and in particular may be derived from the text set out above relating to the first to third aspects of the invention.

According to a fifth aspect of the present invention, there is provided a synthetic joint stabilisation device formed at least partly from a textile (preferably woven) material, the device comprising:
  a first free end;
  a second free end which is opposite the first free end; and
  an integral eye provided at a location which is between the first and second free ends, the eye serving for securing the device to a bone of a patient;

in which the device is at least partly tubular so as to define an internal cavity, said part of the device being of a textile (preferably woven) material;

and in which one of the first and second free ends extends through a wall of the joint stabilisation device and into the internal cavity at a first location, and then extends out of the cavity at a second location which is spaced along a length of the device from the first location, to thereby form a loop which defines the eye.

An assembly may be provided comprising the stabilisation device of the fifth aspect of the invention, and at least one fixation device, for securing the stabilisation device within a tunnel in a bone.

According to a sixth aspect of the present invention, there is provided a synthetic joint stabilisation assembly comprising:

a synthetic joint stabilisation device having:
 a first elongate portion forming a first free end;
 a second elongate portion forming a second free end which is opposite the first free end; and
 an integral eye provided at a location which is between the first and second free ends;
and at least one fixation device;
in which the joint stabilisation device is adapted to be secured to a first bone of the joint by passing the device around the bone and directing the first and second free ends through the eye, to form a loop extending around the bone;
and in which the joint stabilisation device is adapted to be secured to a second bone of the joint using the at least one fixation device, the fixation device adapted to be located in a tunnel in the second bone and to engage at least one of the elongate portions at a location which is spaced along a length of the elongate portion from its free end.

According to a seventh aspect of the present invention, there is provided a method of stabilising a dislocated joint, the method comprising the steps of:

providing a synthetic joint stabilisation device having a first elongate portion forming a first free end, a second elongate portion forming a second free end which is opposite the first free end, and an integral eye provided at a location which is between the first and second free ends;

passing the joint stabilisation device around a first bone of the joint;

directing the first and second free ends of the device through the eye to form a loop extending around the first bone;

applying tension to the device to shorten the loop, thereby securing the device to the first bone;

directing the first free end of the device through a tunnel in a second bone of the joint;

directing the second free end of the device through a tunnel in the second bone;

reducing the first bone relative to the second bone;

applying tension to the first and second elongate portions of the device;

securing the first elongate portion of the joint stabilisation device to the second bone using a fixation device inserted into a mouth of the tunnel in which the first elongate portion is located, the fixation device engaging the first elongate portion at a location which is spaced along the length of said portion from the first free end; and securing the second elongate portion of the joint stabilisation device to the second bone using a fixation device inserted into a mouth of the tunnel in which the second elongate portion is located, the fixation device engaging the second elongate portion at a location which is spaced along the length of said portion from the second free end.

Further features of the joint stabilisation assembly/method may be derived from the text set out elsewhere in this document, and in particular from the text set out above relating to the third and/or fourth aspects of the invention.

It will be understood that the stabilisation device/assembly and method disclosed herein may have other uses than in the stabilisation of a dislocated ACJ, and that the stabilisation device may be used to perform at least part of the function of other damaged tissue, including but not restricted to tendons. The stabilisation device/assembly and method may have a use in stabilisation of an elbow joint, and so of the collateral ligaments at the elbow, as well as repairs of distal biceps tendon avulsion.

Any one of the devices, assemblies and methods defined above may comprise one or more of the features of one or more of the other devices, assemblies and methods disclosed elsewhere in this document. Other devices, assemblies and methods may be provided having features derived from one or more of the devices, assemblies and methods disclosed anywhere in this document.

Embodiments of the present invention will now be described, by way of example only, with reference to the accompanying drawings, in which.

Figure 14:
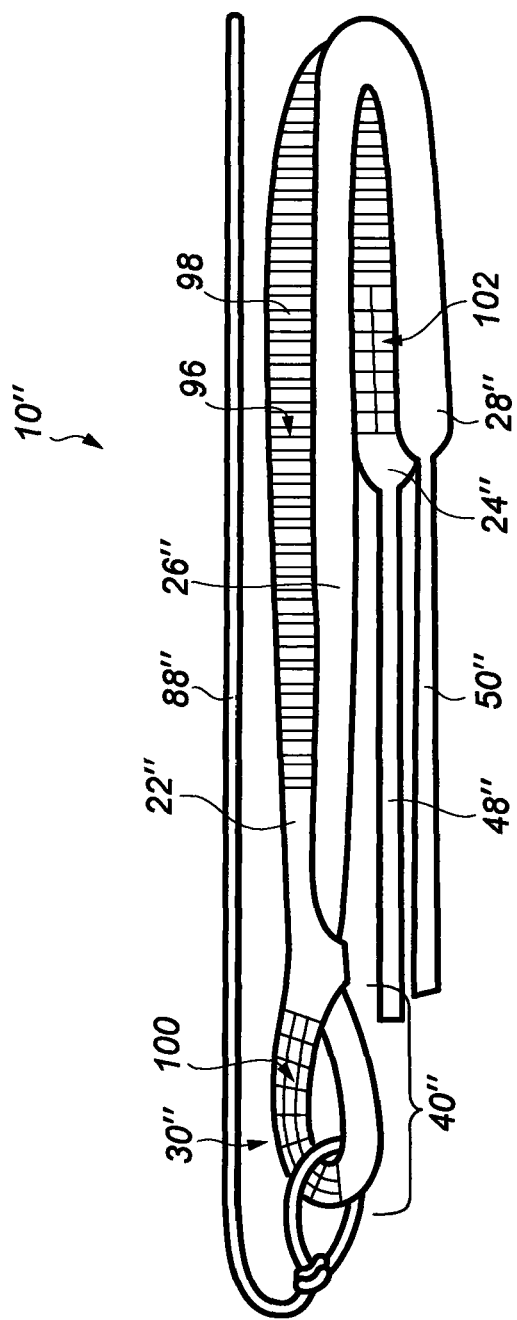
FIG. 14 is a side view of a synthetic joint stabilisation device in accordance with another embodiment of the present invention, which has a use in any of the methods disclosed herein.
Figure 17:
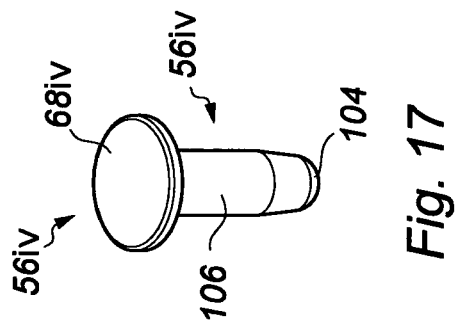
Figure 16:
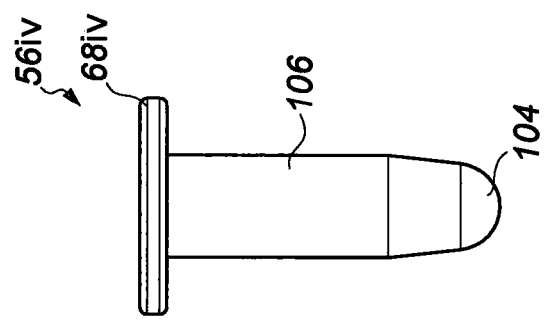

FIGS. 16 and 17 are side and perspective views, respectively, of another embodiment of a fixation device, which may form part of a synthetic joint stabilisation assembly according to an embodiment of the present invention; and FIGS. 18 to 24 are perspective views showing steps in a method of stabilising the ACJ using the synthetic joint stabilisation device of FIG. 14, in accordance with an embodiment of the present invention.

Figure 1:
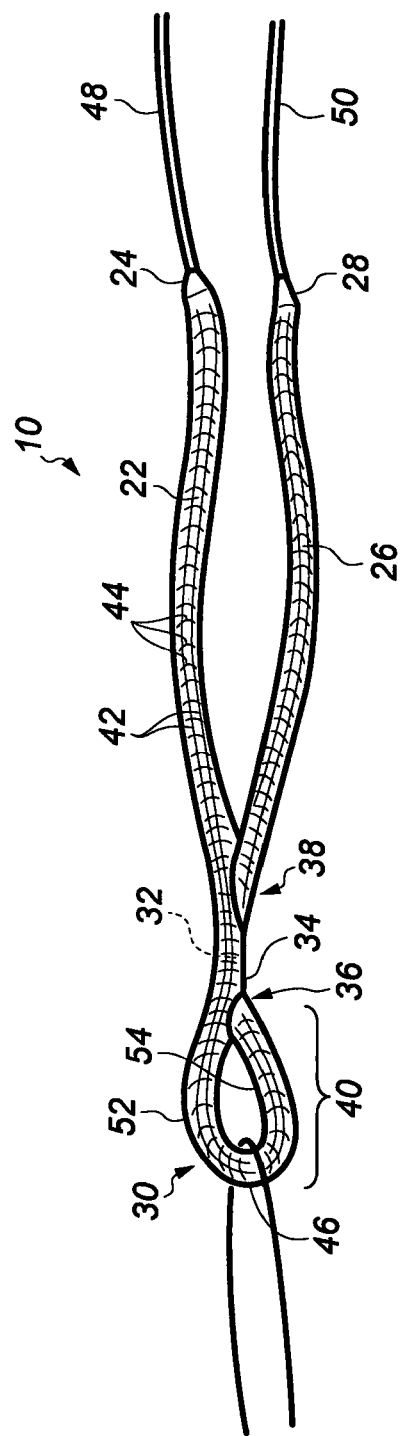
FIG. 1 is a side view of a synthetic joint stabilisation device in accordance with an embodiment of the present invention, which may have a use in a method of stabilising a dislocated ACJ, and which may also form part of a synthetic ACJ stabilisation assembly.

Turning firstly to FIG. 1, there is shown a synthetic joint stabilisation device in accordance with an embodiment of the present invention, the device indicated generally by reference numeral 10. The joint stabilisation device 10 can form part of a synthetic ACJ stabilisation assembly, and may have a use in a method of stabilising a dislocated joint (particularly an ACJ), both of which fall within the scope of the present invention and will be described below. Whilst the joint stabilisation device 10 may form part of such an ACJ stabilisation assembly, and may have a use in such a method, the device may also have uses in other surgical methods/assemblies, and in particular may have a use in the stabilisation of other joints in the body and in the repair of ligaments other than those which are found in the ACJ, and indeed other tissue including but not limited to tendons.

Figure 2:
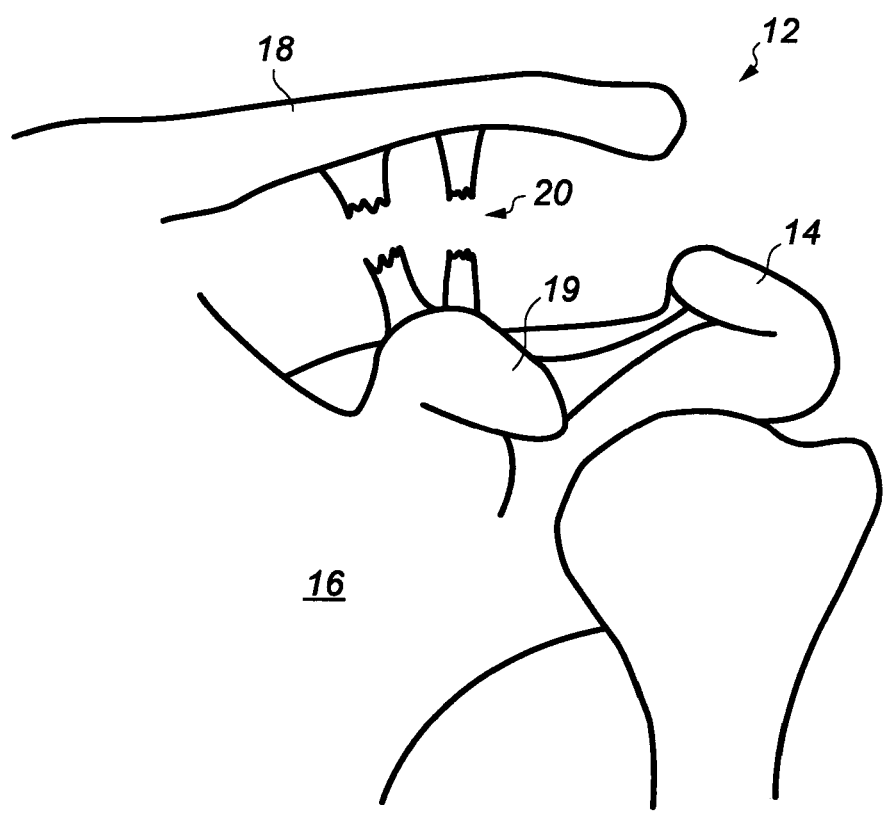
FIG. 2 is a perspective view of a dislocated ACJ.

A dislocated ACJ is shown in the perspective view of FIG. 2. The ACJ is indicated generally by reference numeral 12 and, as outlined above, is the junction between the acromion 14, which is part of the scapula 16, and the clavicle 18. A dislocation of the ACJ has occurred, resulting in the clavicle 18 becoming separated from the acromion 14, due to damage to the ligaments in the ACJ, and particularly damage to the CC ligament and/or the AC ligament. The CC ligament is indicated generally by reference numeral 20, and extends between the clavicle 18 and the coracoid process 19. The ACJ 12 shown in the drawing has suffered a stage acromioclavicular injury, with complete disruption of the AC ligament and the CC ligament 20. Damaged parts of the trapezoid and conoid ligaments, which together form the CC ligament 20, are shown in the drawing. The AC ligament is not shown in the drawing hut, as is well known, extends between a lateral end of the clavicle 18 and the acromion 14.

The joint stabilisation device 10 generally comprises a first elongate portion forming a first free end 24, and a second elongate portion 26 forming a second free end 28 which is opposite (considered along a length of the device) the first free end 24. An integral eye 30 is provided at a location which is between the first and second free ends 22 and 28, and serves for securing the joint stabilisation device 10 to a bone of a patient. The device 10 is at least partly tubular so as to define an internal cavity 32, said part of the device being of a textile (preferably woven) material. One of the first and second elongate portions 22, 26 extends into the internal cavity 32 through a wall 34 of the other one of the first and second elongate portions 22, 26 at a first location 36 along a length of said other portion, and then extends out of the internal cavity 32 at a second location 38 which is spaced along a length of said other portion from the first location, to thereby form a loop 40 which defines the eye 30. In the illustrated embodiment, the second elongate portion 26 extends into the internal cavity 32 through the wall 34 in the first elongate portion 22, and then back out of the cavity through the wall.

Providing a synthetic joint stabilisation device 10 which is at least partly tubular, said part of the device being of a woven material, provides the advantage that warp and weft yarns (or filaments) 42 and 44 of the woven material can easily be separated, so that the second elongate portion 26 can be passed into and out of the internal cavity 32. This facilitates formation of the loop 40 and so the eye 30. In addition, it is easy to adjust a dimension of the loop 40 during manufacture of the joint stabilisation device, because the woven structure of the material facilitates sliding movement between the elongate portions 22 and 26.

As can be seen from FIG. 1, the second elongate portion 26 is drawn through the internal cavity 32 so that a distance between an apex 46 of the eye 30 and each of the free ends 24, 28 is approximately equal. The elongate portions 22 and 26 thus effectively extend from the apex 46 to the respective free ends 24, 28. The elongate portions 22 and 26 are then preferably secured against movement relative to one another, to prevent the second elongate portion 26 from moving within the internal cavity 32, thereby fixing a dimension of the loop 40 and so of the eye 30. This may be achieved in numerous ways, including by stitching, suturing, whipping or fusing the elongate portions 22 and 26 together, or by a combination of two or more such techniques. However, in certain circumstances, it may be desirable to provide a joint stabilisation device 10 in which movement of the elongate portions 22, 26 relative to one another remains possible (in particular sliding movement of the second elongate portion 26 within the internal cavity 32), to facilitate adjustment of a dimension of the loop 40, and so the eye 30, during a procedure to implant the device 10.

In the preferred embodiment, the joint stabilisation device 10 is entirely of a woven material, and is tubular over a majority of its length (and optionally over an entirety of its length). The device 10 may also be closed at the first and second ends 24 and 28. Closing the ends 24 and 28 (e.g. by flattening the tubular structure, and stitching or fusing opposed portions of the wall 34 together) provides a secure location for the attachment of pulling sutures 48 and 50, which are used during implantation of the joint stabilisation device 10, as will be described below. The device 10 is typically a textile, formed from a woven tubular structure, which is formed so as to be tubular during the weaving process. Whilst weaving is preferred, other textile manufacturing techniques may be employed, particularly braiding or embroidering. The pulling sutures 48 and 50 can optionally be coupled together, or a single pulling suture (not shown) used which is attached to both of the ends 24 and 28.

The eye 30 is an integral eye, in that a material forming the first and second elongate portions 22, 26 also forms the eye. The eye 30 may also/alternatively be considered integral in that the first and second elongate portions 22, 26 and the eye 30 can be formed from a single elongate structure, i.e. the woven tubular structure. The eye 30 comprises parts of the first and second elongate portions 22 and 26, and in particular comprises parts 52 and 54, respectively, of the first and second elongate portions 22 and 26 which extend from the apex 46 of the eye 30 to the first location 36.

The formation of a synthetic joint stabilisation device 10 having an integral eye 30 facilitates use of the device in surgical procedures. In particular, and as will be described below, the free ends 24 and 28 of the joint stabilisation device 10 can be passed around a bone and then through the eye 30, to form a loop which can extend around the bone. This can serve for anchoring the device 10 to the bone in question. It is also feasible that the eye 30 could be passed directly over an end of a bone; that the eye 30 could receive a fixation device such as a fixation screw, for securing the joint stabilisation device 10 to a bone; that the eye 30 could receive a loop or suture of another material, which is used to pass the device 10 around bone or through a bone tunnel; that the eye 30 could receive a loop or suture of another material, which is used to secure the device 10 to bone; and/or that the eye 30 could receive a restraining element such as a bone toggle or button which is adapted to be position at the end of a bone tunnel in which the device 10 is located, so that the device is effectively suspended from an external surface of the bone surrounding a mouth of the tunnel.

The present invention also provides a synthetic joint stabilisation assembly comprising the synthetic joint stabilisation device 10 shown in FIG. 1 and described above, and at least one fixation device, for securing at least one of the first and second elongate portions 22 and 26 of the joint stabilisation device within a tunnel in a bone. In the case of an ACJ stabilisation procedure, the tunnel would typically be formed in the clavicle 18. Suitable bone fixation devices are shown in the perspective views of FIGS. 3, 4 and 5, and given the reference numerals 56, 56' and 56", respectively. The fixation devices 56 to 56" and their function will be described in more detail below.

As mentioned above, the synthetic joint stabilisation device 10 has a particular use in the stabilisation of a dislocated ACJ. The joint stabilisation device 10 may facilitate repair of a damaged CC ligament 20. However and as will be described below, the joint stabilisation device 10 may facilitate repair of a damaged CC ligament 20 and a damaged AC ligament, and may facilitate repair or damaged sterno-clavicular ligaments.

Figure 6:
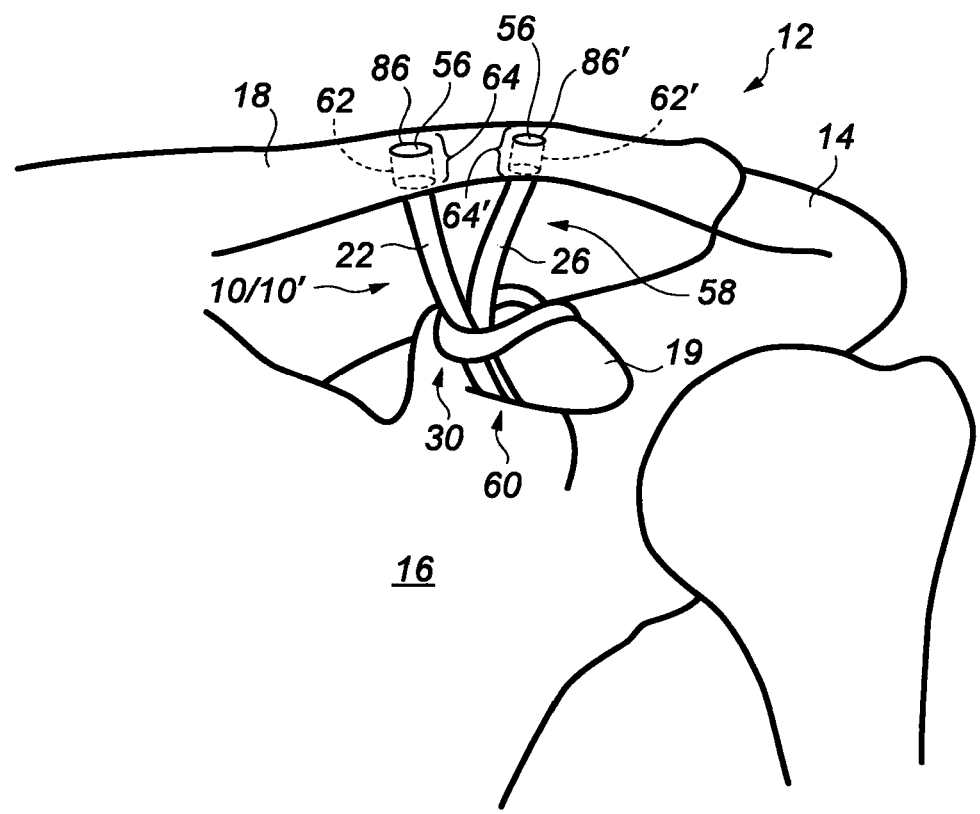
FIG. 6 is a perspective view of the dislocated ACJ of FIG. 2, showing steps in a method of stabilising the ACJ using a synthetic joint stabilisation device, in accordance with an embodiment of the present invention.
Figure 7:
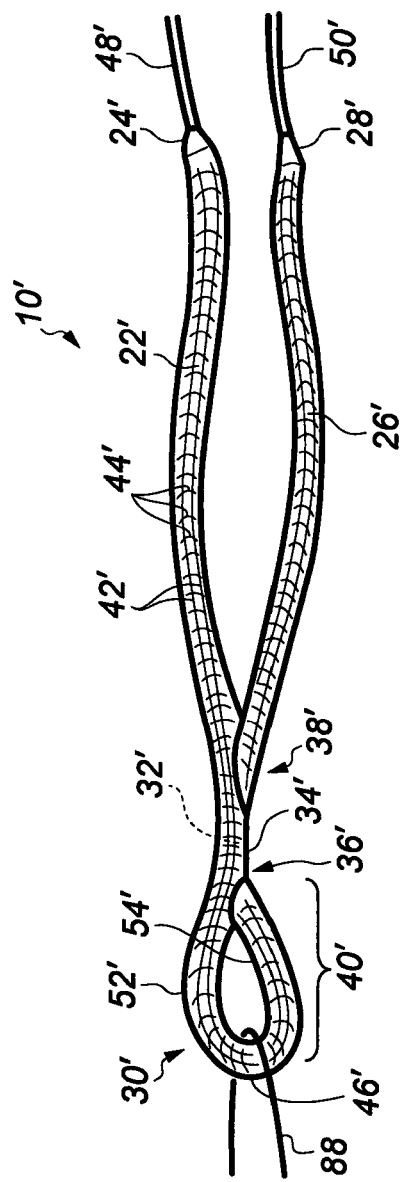
FIG. 7 is a side view of a synthetic joint stabilisation device in accordance with another embodiment of the present invention, which has a use in the method of FIG. 6, and which forms part of a synthetic ACJ stabilisation assembly according to an embodiment of the present invention.

FIG. 6 illustrates steps in a method of stabilising the ACJ using a synthetic joint stabilisation device, and shows a synthetic ACJ stabilisation assembly, indicated generally by reference numeral 58 and comprising a synthetic joint stabilisation device which may be the device 10 of FIG. 1, but is shown as a device 10' (FIG. 7), in accordance with an embodiment of the present invention.

The synthetic joint stabilisation device 10', in this embodiment of ACJ stabilisation assembly 58, need not necessarily comprise all of the features of the joint stabilisation device 10 shown in FIG. 1 and described above. Like components of the joint stabilisation device 10' with the joint stabilisation device 10 share the same reference numerals, with the addition of the suffix '. In general terms, the ACJ stabilisation assembly 58 comprises the synthetic joint stabilisation device 10' and at least one fixation device, which may be any one of the devices 56 to 56" shown in FIGS. 3 to 5. The device 56 is, however, shown in FIG. 6.

The joint stabilisation device 10', in this embodiment, has a first elongate portion 22' forming a first free end 24', a second elongate portion 26' forming a second free end 28' which is opposite the first free end 24', and an integral eye 30' provided at a location which is between the first and second free ends. The joint stabilisation device 10' is adapted to be secured to the coracoid process 19 of the ACJ 12 by passing the joint stabilisation device around the coracoid process and directing the first and second free ends 24' and 28' through the eye 30', to form a loop 60 extending around the coracoid process.

The joint stabilisation device 10' is adapted to be secured to the clavicle 18 using the at least one fixation device 56, the fixation device adapted to be located in a tunnel 62 in the clavicle and to engage at least one of the elongate portions 22' and 26' at a location 64 which is spaced along a length of the elongate portion from its free end 24',28'. As will be described below, sections of the elongate portions 22' and 26' including the free ends 24' and 28' are typically severed following securement to the clavicle 18. It will be understood that FIG. 6 shows the joint stabilisation device 10' following such severing.

The synthetic ACJ stabilisation assembly 58 of the present invention provides the advantage that a length of the synthetic joint stabilisation device 10' is not fixed prior to implantation. A surgeon can select a desired length of the joint stabilisation device by securing it relative to a bone (in particular the clavicle 18) at a location or locations which are spaced along a length of the device from the first and/or second free ends 24' and 28'. The synthetic joint stabilisation device 10' can therefore be provided of a length which is greater than the likely maximum length required for an ACJ stabilisation procedure employing the device, with the surgeon setting the final length during the implantation procedure.

Preferably, the joint stabilisation device 10' shares all of the further features of the joint stabilisation device 10 shown in FIG. 1 and described above, and so is at least partly tubular so as to define an internal cavity, said part being of a woven material. The joint stabilisation device 10' is thus preferably manufactured according to the technique described above, and so will not be described in more detail here.

The assembly 58 shown in FIG. 6 in fact comprises a first fixation device 56 adapted to be located in a first tunnel 62 in the clavicle, and to engage the first elongate portion 22' of the joint stabilisation device 10' at the location 64 spaced from its free end 24'; and a second such fixation device 56 adapted to be located in a second tunnel 62' in the clavicle, and to engage the second elongate portion 26' of the joint stabilisation device at a location 64' which is spaced along a length of said portion from its free end 28'. It will therefore by understood that each elongate portion 22' and 26' of the joint stabilisation device 10' is located in separate tunnels 62 and 62' in the clavicle 18, and secured using respective fixation devices 56.

Figure 8:
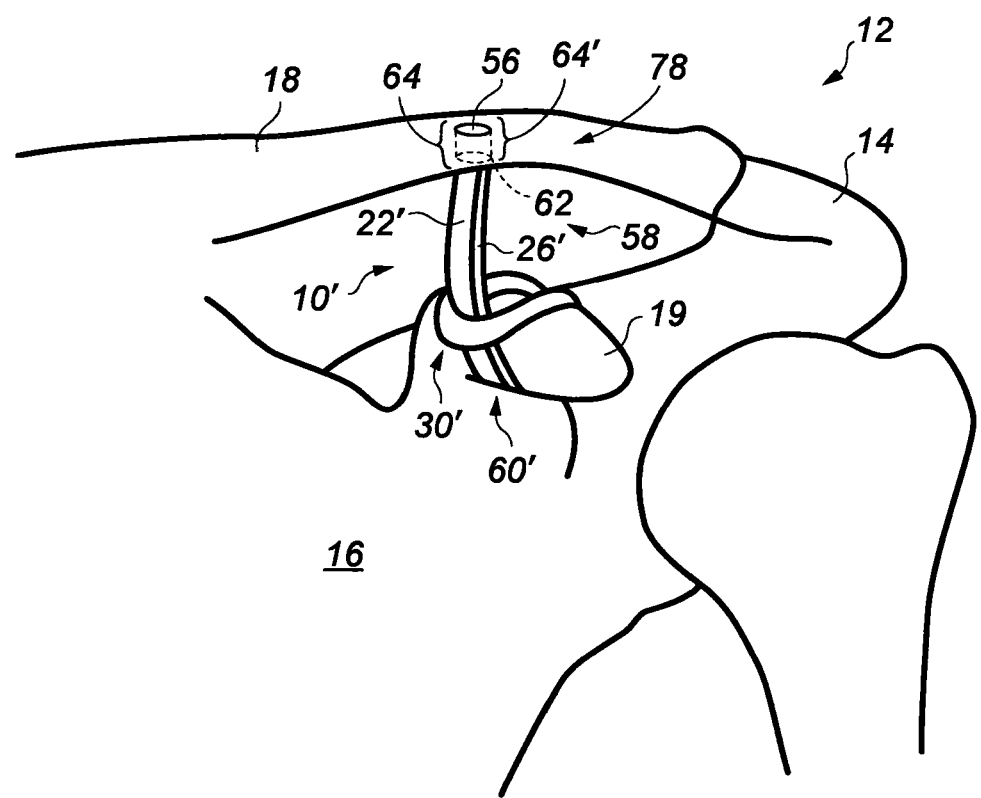
FIGS. 8 to 13 are perspective views of a dislocated ACJ, showing steps in methods of stabilising the ACJ using the synthetic joint stabilisation device of FIG. 7, in accordance with further embodiments of the present invention.

A variation on this technique is shown in FIG. 8, in which a single fixation device 56 is provided which is adapted to be located in the tunnel 62 in the clavicle 18, and to engage the first and second elongate portions 22' and 26' of the joint stabilisation device 10' at locations 64 and 64' which are spaced along lengths of said portions from their free ends 24' and 28'. It will therefore by understood that both elongate portions 22' and 26' of the joint stabilisation device 10' are located in a common tunnel 62 in the clavicle 18, and secured using a common fixation device 56.

The fixation devices 56, 56' and 56'" will now be described in more detail, with reference once again to FIGS. 3, 4 and 5. Like components of the fixation devices 56, 56' and 56" share the same reference numerals with the appropriate suffix' or".

Figure 3:
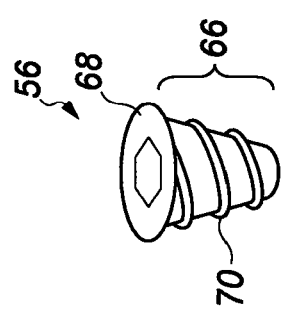

The fixation device 56 shown in FIG. 3 comprises a locating part 66 adapted to be located in the tunnel 62, and an abutment part 68 adapted to abut the elongate portion 22' and/or 26' to secure it to the clavicle 18. The fixation device 56 is a threaded device, such as a screw, having an external thread 70 which is adapted to engage a wall of the tunnel 62 to secure the device within the tunnel, and to clamp or trap the elongate portion 22' and/or 26' between an outer surface of the device and the wall of the tunnel. The abutment part 68 is provided by a head of the device.

Figure 4:
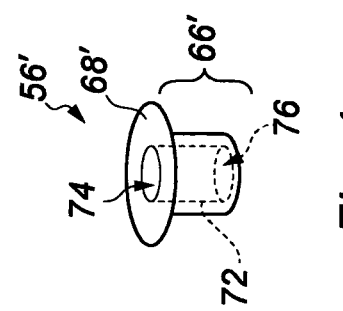

The fixation device 56' shown in FIG. 4 comprises a passageway 72 extending through the device, for receiving the elongate portion 22' and/or 26'. The passageway 72 extends through a locating portion 66' of the device 56', and is open at its ends 74 and 76 so that the elongate portion 22' and/or 26' can extend through the passageway. The fixation device 56' is a generally annular member such as a collar, in which locating portion 66' takes the form of a tube and the abutment portion 68' takes the form of a flange which is adapted to abut an outer surface 78 (FIG. 8) of the clavicle 18, to retain the device 56' in the tunnel 62. The fixation device 56' engages an enlarged dimension section of the elongate portion 22' and/or 26' to secure it relative to the clavicle 18, by abutment between the flange 68' and the enlarged dimension section. As will be described below, the enlarged dimension section will typically be a knot formed in said elongate portion 22' or 26', and/or between the elongate portions.

Figure 5:
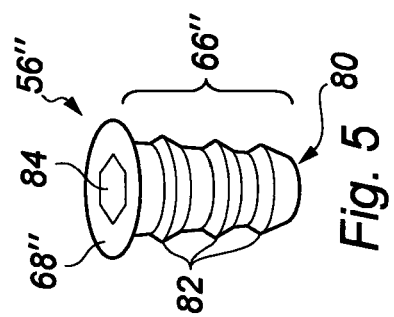
FIGS. 3, 4 and 5 are perspective views of different embodiments of fixation devices, which may form part of a synthetic joint stabilisation assembly according to an embodiment of the present invention comprising the synthetic joint stabilisation device of FIG. 1, which may have a use in a method of stabilising a dislocated ACJ, and which may form part of a synthetic ACJ stabilisation assembly.

The fixation device 56" shown in FIG. 5 takes the form of a plug which can have a partly solid cross-section, and which is adapted to provide an interference fit with the bone tunnel 62, to clamp or trap the elongate portion 22' and/or 26' between an outer surface of the plug and a wall of the tunnel. The plug 56" may taper from a proximal head, which defines an abutment portion in the form of a flange 68", towards a distal end 80. The plug 56" includes enlarged diameter annular sections 82, which provide the interference fit with the wall of the tunnel 62. The plug 56" includes an aperture 84 which can receive a driving tool (not shown) that is used to impart an impact force on the plug to drive it into the tunnel 62.

In each case, the abutment portions 68 to 68" of the fixation devices 56 to 56" take the form of flanges which abut the surface 78 of the clavicle 18. Implantation of the joint stabilisation device 10' involves tensioning the elongate portions 22' and 26', the tensile load being directed towards the coracoid process 19, and is resisted by contact between the flanges 68 to 68" and the surface 78, to retain the devices within the tunnel 62.

A method of stabilising a dislocated ACJ, employing the stabilisation assembly 58 discussed above, will now be described, referring initially to FIG. 6. As will be understood by persons skilled in the art, the method may involve an open surgical procedure, but preferably involves a minimally invasive, arthroscopic procedure. In either case, suitable well-known preparatory steps will be carried out to gain access to the area of the ACJ, which will not be described in detail herein. The method generally comprises the following steps.

The joint stabilisation device 10' is passed around the coracoid process 19 of the ACJ 12. The first and second free ends 24' and 28' of the joint stabilisation device 10' are then directed through the eye 30', to form the loop 60, which extends around the coracoid process 19. Tension is then applied to the joint stabilisation device 10' to shorten the loop 60, thereby securing the device to the coracoid process 19. The first free end 24' of the joint stabilisation device 10' is directed through the tunnel 62 in the clavicle 18, and the second free end 28' through the tunnel 62'. This is achieved with the assistance of the pulling sutures 48' and 50'. The clavicle 18 is reduced relative to the coracoid process 19, which may be performed with the assistance of a suitable instrument, and/or via manipulation of the joint stabilisation device 10'.

Tension is then applied to the first and second elongate portions 22' and 26' of the joint stabilisation device 10'. The first elongate portion 22' of the joint stabilisation device 10' is secured to the clavicle 18, using the fixation device 56, which is inserted into a mouth 86 of the tunnel 62 in which the first elongate portion 22' is located. The fixation device 56 engages the first elongate portion 22' at the location 64, which is spaced along the length of said portion from the first free end 24'. The second elongate portion 26' of the joint stabilisation device 10' is similarly secured to the clavicle 18 using a second fixation device 56 inserted into a mouth 86' of the tunnel 62' in which the second elongate portion 26' is located. The second fixation device 56' engages the second elongate portion 26' at the location 64', which is spaced along the length of said portion from the second free end 28'.

The result of this is that the clavicle 18 is reduced relative to the coracoid process 19, and stabilised by the synthetic joint stabilisation device 10'.

The method will now be described in more detail. Variations will also be discussed.

The method shown in FIG. 6 and described above is an open technique, involving CC repair with the assistance of two tunnels 62 and 62' in the clavicle 18. A hook instrument (not shown) facilitates passing of the joint stabilisation device 10' around the coracoid process 19. It may be preferable to place the joint stabilisation device 10' in the clavicle with two tunnels 62 and 62', to create an anatomical repair. However, a single tunnel technique for the clavicle could also be used, as shown in FIG. 8.

Firstly, a 3 to 5 cm incision is made in a sagittal plane, extending up from the coracoid process 19 over the clavicle 18. This is preferred over transverse incisions, which can lead to poor scars. The medial 5 cm of the deltoid muscle (not shown) is divided off the clavicle, and reflected laterally creating a flap for later reattachment. The ACJ 12, lateral part of the clavicle 18 and coracoid process 19 are exposed. The tunnels 62 and 62' are made by forming two oblique drill holes in the lateral clavicle, either side of the coracoid process 19, using a 3 mm drill bit. A tubular ACJ hook instrument is loaded with a wire (not shown) and is passed medial to lateral under the coracoid process 19. The wire is pushed out of the hook to expose the eyelet 30' of the joint stabilisation device 10' at its end. A lead suture 88 is placed through the eyelet 30' and the hook instrument is retracted to leave the lead suture 88 under the coracoid process 19. The lead suture 88 is pulled to implant the looped end (eyelet 30') of the joint stabilisation device 10' under and around the coracoid process 19.

Figure 9:
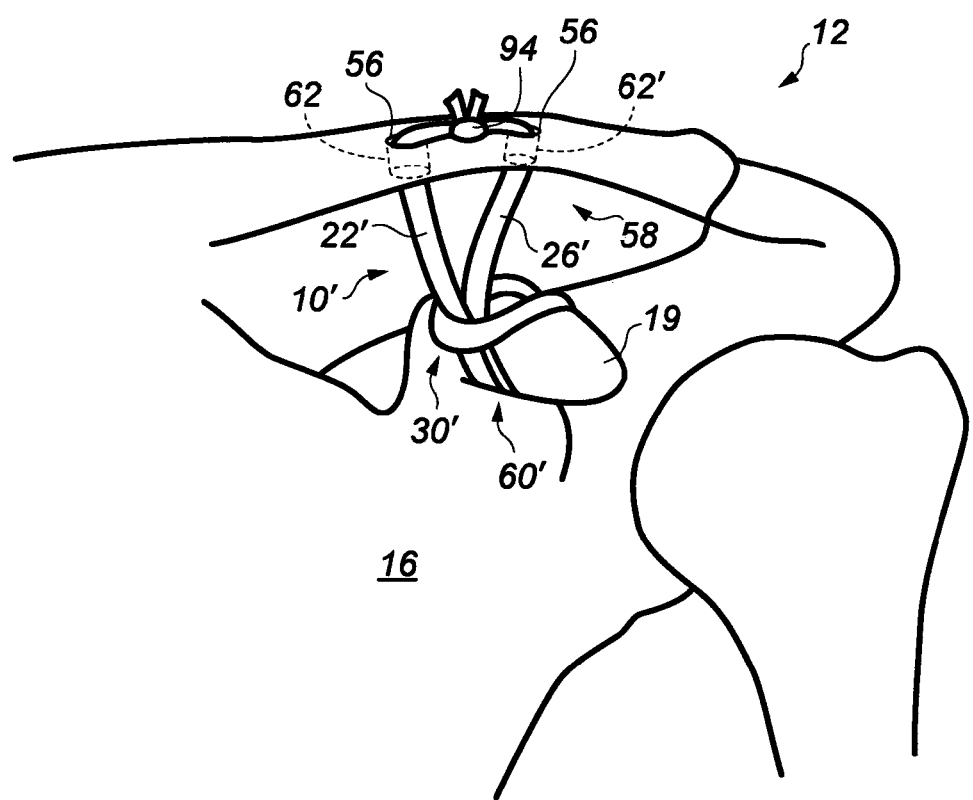

Next, the two free ends 24' and 28' of the joint stabilisation device 10' are passed through the opposite looped end (eyelet 30') of the device, and the ends are then tensioned to seat the device to the coracoid process 19. Wire loops or needles (not shown) on ends of the pulling sutures 48' and 50' are passed through the clavicular tunnels 62 and 62' to act as leaders. The two suture ends of the ligament are each looped over the wire/suture and the device pulled through each tunnel 62, 62'. Each end of the joint stabilisation device 10' is pulled to create tension, whilst holding the reduced ACJ. A bone reduction forceps (not shown) can be used to assist with the reduction, with one side under the coracoid process 19 and the other over the lateral part of the clavicle 18. Each end of the joint stabilisation device 10' is then fixed in the clavicle tunnel with the interference screws 56 and remaining sections of the elongate portions 22' and 26' of the device 10' (including the free ends 24' and 28') are severed. A variation on this method is shown in FIG. 9, in which the elongate portions 22' and 26' are knotted together by a knot to form a knot 94 or, in a further alternative, overlapped and stitched together. This provides a secondary fixation. In either case, surplus sections of the joint stabilisation device 10' are cut off, by severing remaining sections of the elongate portions 22' and 26' of the device 10' (including the free ends 24' and 28'). The incision is then closed by suturing together the trapezo-deltoid fascia and reattaching the lateral deltoid.

Returning to FIG. 8, there is shown an open technique, CC repair, using one tunnel. The method involves making the same incision, and the same approach and coracoid threading technique for the joint stabilisation device 10' and closure is used, as described for the two tunnel technique of FIG. 6. The difference in this embodiment of the method is that one oblique drill hole is made with a larger (e.g. 4.5 mm) drill bit centrally (AP direction) in the lateral part of the clavicle 18 above the coracoid process 19, to form the single tunnel 62. The two free ends 24' and 28' of the joint stabilisation device 10' are then both passed through the bone tunnel 62, again facilitated by wire loops or needle sutures. Each end 24' and 28' of the joint stabilisation device 10' is pulled to part the device and create tension, whilst holding the reduced ACJ 12. The single screw 56 is then inserted between the two ends of the device.

Figure 10:
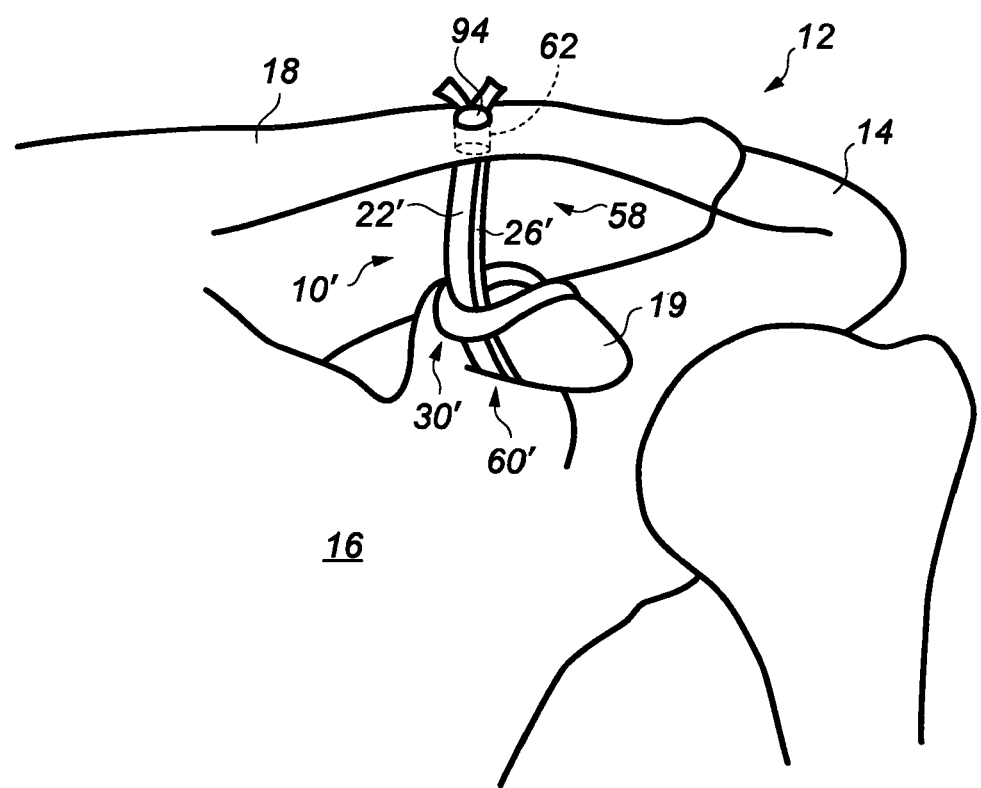
Figure 11:
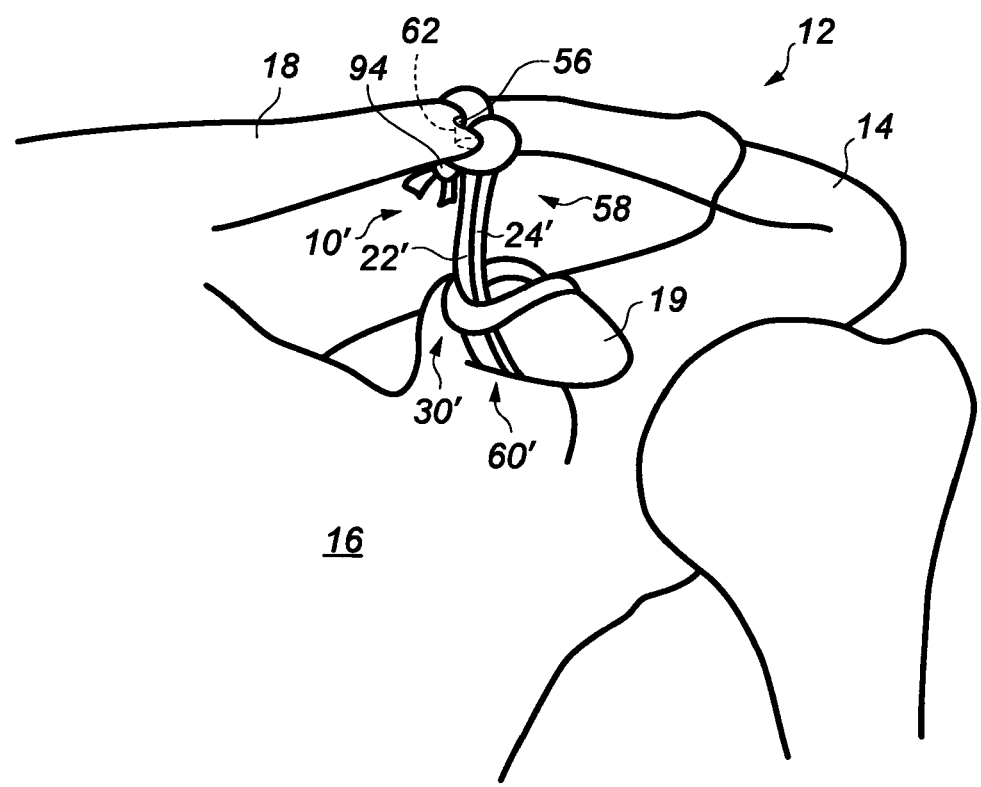

A variation on this method is based on the single tunnel method and is shown in FIG. 10, in which the elongate portions 22' and 26' are knotted together over the top of the screw 56 to form a knot 94 which provides secondary fixation. A further variation is shown in FIG. 11, in which one of the elongate portions 22' and 26' is passed posteriorly around the clavicle 18, and the other anteriorly. The elongate portions 22' and 26' are then knotted underneath the clavicle 18, to form a knot 94.

Figure 12:
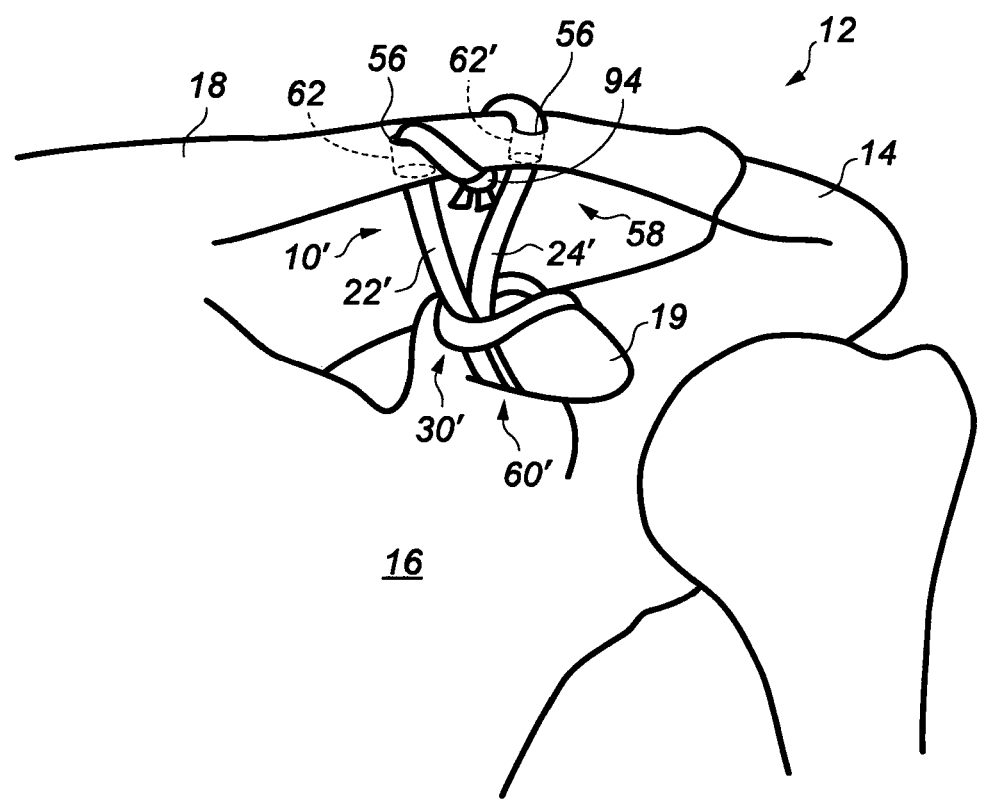

FIG. 12 shows a variation on the method disclosed in FIG. 6, which similarly involves passing one of the elongate portions 22' and 26' posteriorly around the clavicle 18, and the other anteriorly and then knotting them together underneath the clavicle 18, forming a knot 94.

Figure 13:
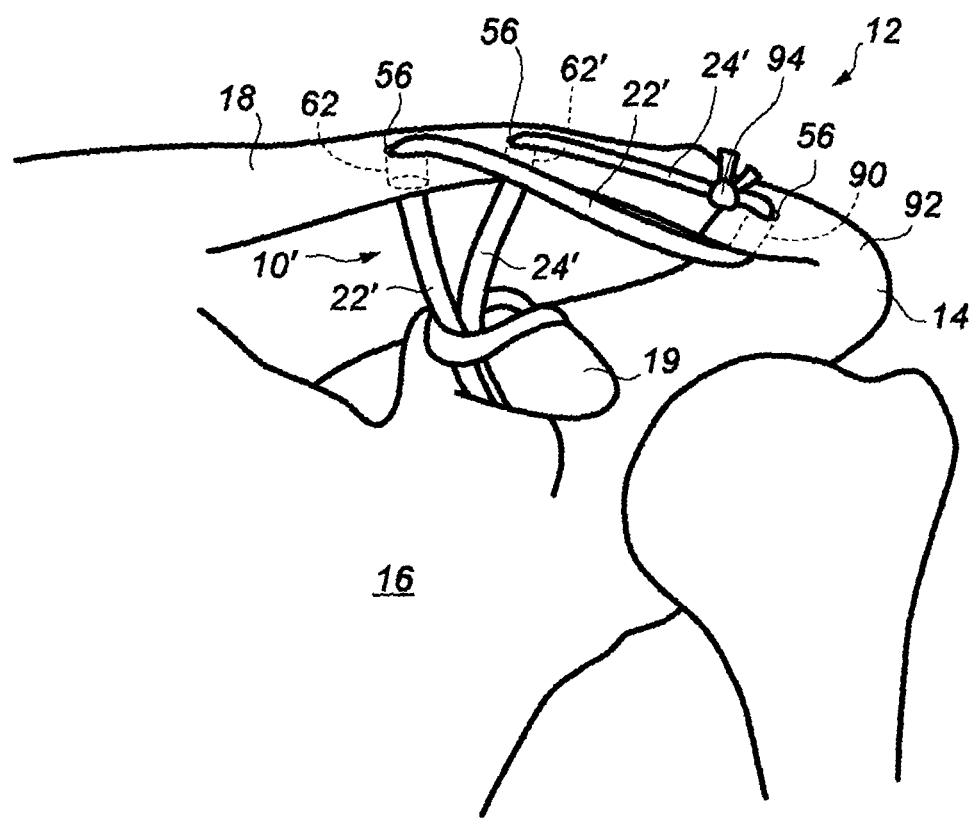

Turning now to FIG. 13, there is shown an open technique, CC and AC repair. This may be accomplished whether a one or two tunnel method is used as described above. In this embodiment, a single 3 mm bone tunnel 90 is placed in the acromion 14. After clavicle fixation is completed, the two excess sections of the elongate portions 22' and 26' of the joint stabilisation device 10' are passed laterally, to repair the ACJ 12. One of the free ends 24' and 28' of the device 10' (e.g. a medially located end) is passed under the acromion 14 and through the tunnel 90, to emerge on a superior surface 92 of the acromion 14. Tunnel passing is facilitated by wire loops or needle sutures. A third screw 56 can be placed in the tunnel 90, if desired, to secure the elongate portion 22',26' of the joint stabilisation device 10' which extends through the tunnel 90. The other one of the free ends 24' and 28' is passed on the anterior surface of the clavicle 18 to the ACJ 12. The two elongate portions 22' and 26' ends of the joint stabilisation device 10' are then knotted over the ACJ, again forming a knot 94.

Alternatives to the above disclosed methods include knotting the joint stabilisation device ends 24' and 28' between the clavicle screws 56 prior to performing the AC repair; an inferior placement of an AC knot; no screw in the acromion 14; using a larger tunnel, through which both ends 24' and 28' of the joint stabilisation device 10' are passed, one threaded top to bottom (superior-inferior), the other bottom to top (inferior-superior), and secured with a fixation screw 56.

Turning now to FIG. 14, there is shown a synthetic joint stabilisation device in accordance with another embodiment of the present invention, the device indicated generally by reference numeral 10". Like components of the joint stabilisation device 10" with the device 10 of FIG. 1, or with the device 10' of FIG. 7, share the same reference numerals with the addition of the suffix", or with the suffix' replaced by the suffix" as appropriate. Only the substantive differences between the joint stabilisation device 10" and the devices 10 and 10' will be described herein in detail.

The joint stabilisation device 10" differs from the devices 10 and 10' in that it comprises at least one indicator, indicated generally by reference numeral 96 in the drawing. The indicator 96 is associated with a part of the device which, in the illustrated embodiment, is one of first and second elongate portions 22" and 26" of the device 10", and in particular the first elongate portion 22". The indicator 96 facilitates identification of the second elongate portion 22" during use and during implantation of the device within a body of a patient. In particular, the indicator 96 assists a surgeon in identifying the elongate portions 22" and 26" so that he or she knows which one of the elongate portions to apply tension to, in order to reduce the dimension of a loop 40" forming an eye 30" of the device 10". As will be understood, such may occur following passage of free ends 24" and 28" through the eye 30", in a procedure to implant the stabilisation device 10" of the type described above.

In the illustrated embodiment, the indicator 96 is a visual indicator having a visual characteristic which can be easily identified by the surgeon during implantation of the device 10". In particular, the indicator 96 may be formed by providing a part or parts of the device 10" with a colour which is different from at least one other part, or parts of the device. For example, the device 10" (and in this embodiment the first elongate portion 22") may comprise coloured bands 98. Where the device 10" is textile and in particular woven, the bands 98 may be formed integrally during the weaving process, by providing a suitably coloured yarn in the weave.

The device 10" can comprise a plurality of indicators, each indicator associated with a different part of the device, facilitating identification of the different parts of the device (associated with the respective indicator). In the illustrated embodiment, the device 10" comprises the indicator 96, which forms a first indicator having a first indicator characteristic, and at least one second indicator having a second characteristic which is different from the first characteristic. The illustrated device 10" comprises two such second indicators 100 and 102, which facilitate identification of different parts of the device. The device may comprise a second indicator 100 associated with the integral eye 30" (facilitating identification of the eye), and a second indicator 102 associated with at the free ends 24" (facilitating identification of said end).

It will be appreciated that the different characteristics of the first indicator 96, and the second indicators 100 and 102, may be provided in numerous different ways. Where the device 10" is textile and in particular woven, the different characteristics may be achieved during the weaving process, for example by providing areas of different density, and/or by providing suitable, differently coloured yarns in the weave. In the case of the provision of areas which are coloured and of different density, the greater density weave may provide a stronger colour indication, facilitating identification during implantation.

In the illustrated embodiment, the first 96 and second indicators 100, 102 are all formed by providing yarns of the same colour in the weave. However, the second indicators 100 and 102 are of greater density, this being achieved by employing a greater number of yarns (which may be warp and/or weft yarns) per square unit area.

It will be understood that the number and arrangement of indicators provided on the device 10" may be varied as desired, to facilitate identification of respective parts of the device.

Figure 15:
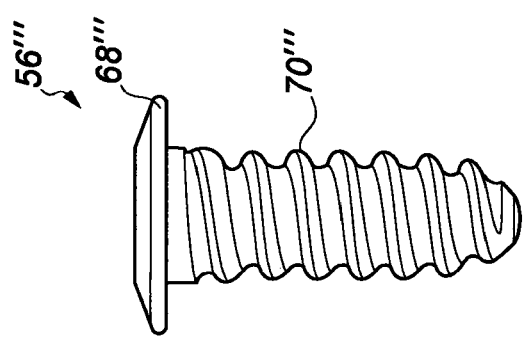
FIG. 15 is a side view of another embodiment of a fixation device, which may form part of a synthetic joint stabilisation assembly according to an embodiment of the present invention.

Turning now to FIG. 15, there is shown a side view of a fixation device 56' which may form part of any one of the stabilisation assemblies disclosed herein. The fixation device 56''' is essentially a variation on the fixation device 56 shown in FIG. 3. Like components of the fixation device 56''' with the device 56 of FIG. 3 share the same reference numerals, with the addition of the suffix'''. The fixation device 56' differs from the device 56 in that it has a different threadform 70''' and a differently shaped abutment portion 68''', in the form of a chamfered head. The chamfered head 68''' restricts the likelihood of damage to the stabilisation device 10, 10' or 10" during use, through contact with the head.

FIGS. 16 and 17 are side and perspective views of a fixation device 56$^{iv}$ which may form part of any one of the stabilisation assemblies disclosed herein. The fixation device 56''' is essentially a variation on the fixation device 56'' shown in FIG. 5. Like components of the fixation device 56$^{iv}$ with the device 56'' of FIG. 5 share the same reference numerals, with the suffix'' replaced by the suffix$^{iv}$.

The fixation device 56 is a plug, and differs from the plug 56'' in that it is at least partly tapered. In the illustrated embodiment, the plug 56$^{iv}$ has a tapered leading end or nose 104, which facilitates insertion into a bone tunnel, and which may reduce a likelihood of damaging the stabilisation device during insertion of the fixation device into the tunnel. The plug 56$^{iv}$ has a main plug portion 106, which serves for clamping or trapping one or both elongate portions of the stabilisation device (as appropriate) within the tunnel. The min plug portion 106 is generally cylindrical, of a substantially uniform diameter, and substantially free from projections so that it is smooth-sided. The plug 56$^{iv}$ has an abutment portion 68$^{iv}$ in the form of a head which, in this embodiment, does not have an aperture for a driving tool. Instead, the head 68$^{iv}$ is flat, providing an impact surface for a tool such as a tamp or hammer, which can be used to insert the plug 56$^{iv}$ into the bone tunnel.

Turning now to FIGS. 18 to 24, there are shown steps in a method of stabilising the ACJ 12 employing the stabilisation device 10''. The method corresponds in many ways to that shown and described in FIGS. 8, 10 and 11, but will be briefly outlined.

Figure 18:
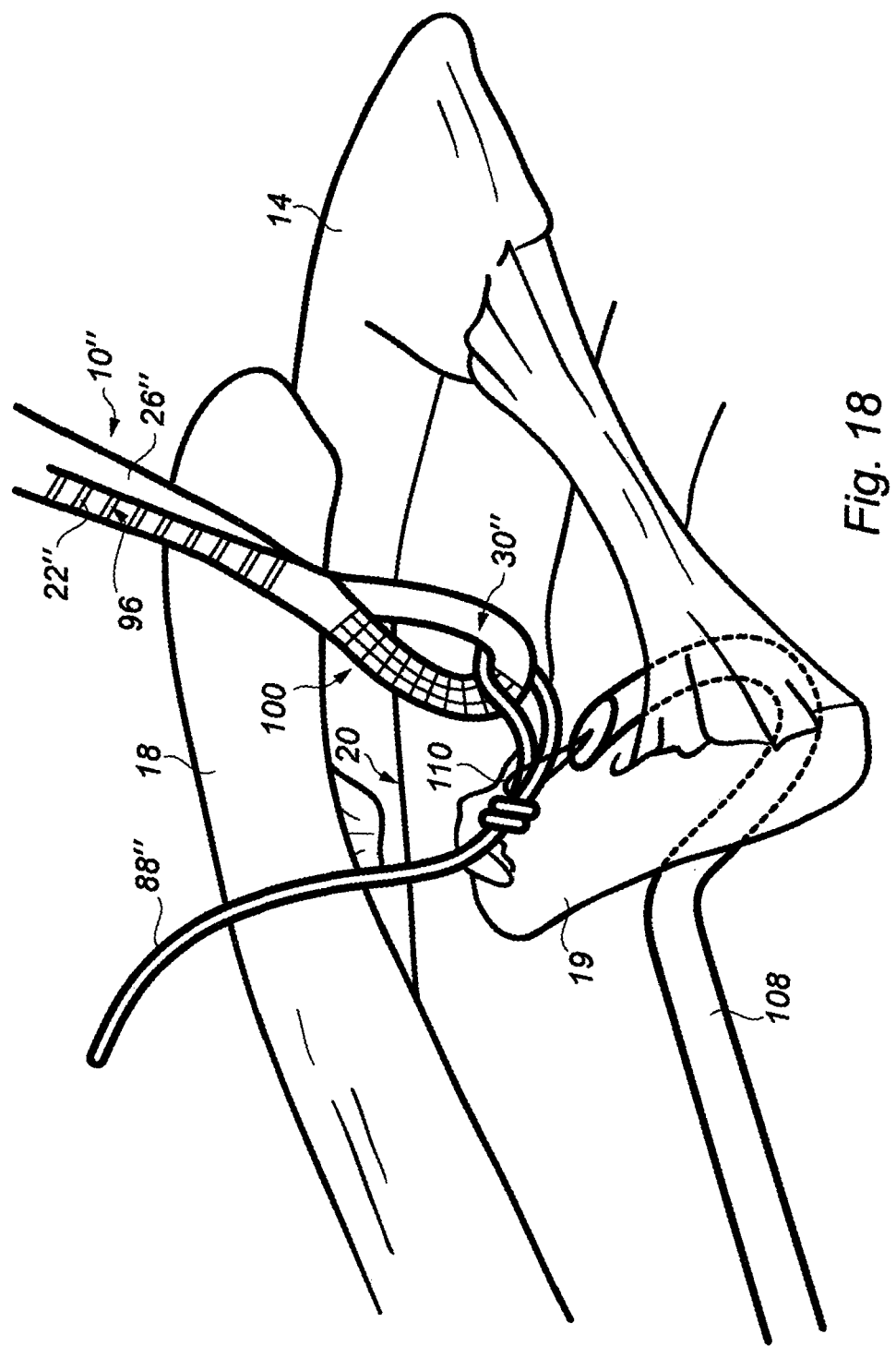
Figure 19:
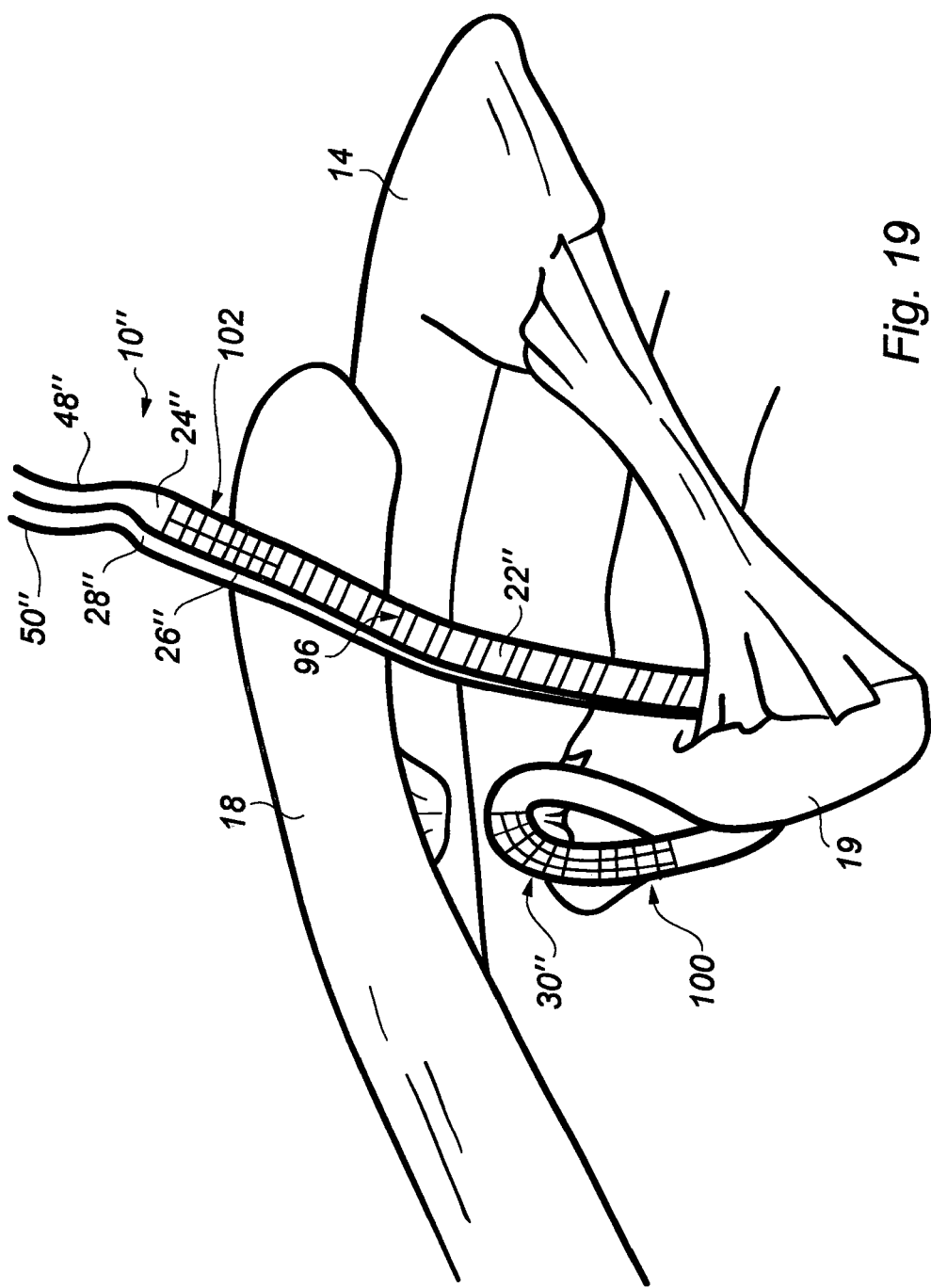
Figure 20:
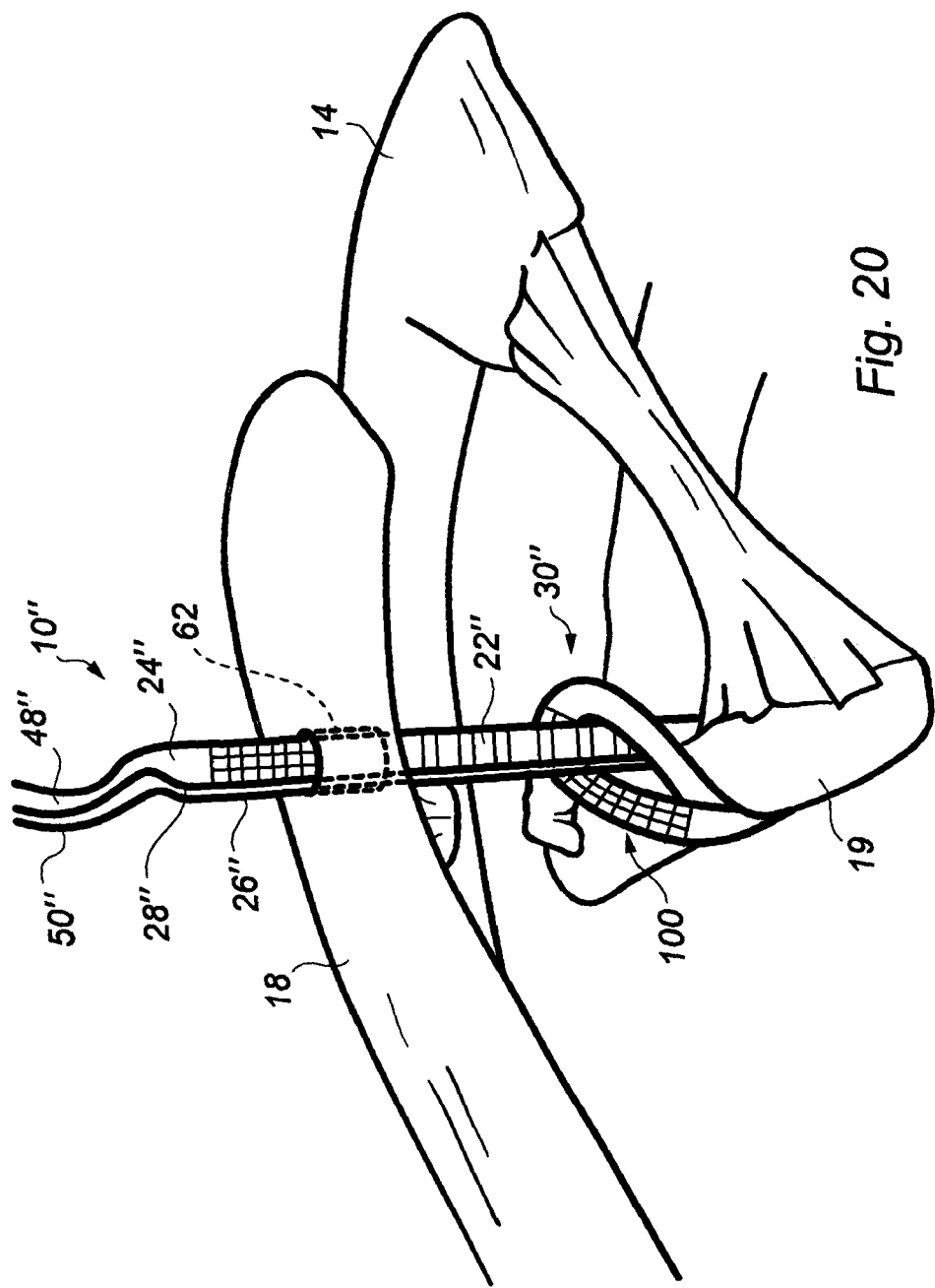

As shown in FIG. 18, a hook instrument 108 is used to pass the stabilisation device 10'' around the coracoid process 19, via a loop 110 which receives a lead suture 88''. The stabilisation device 10'' is manipulated to the position shown in FIG. 19. The two free ends 24'' and 28'' of the stabilisation device 10'' are then passed through the opposite looped end (eyelet 30') of the device, and the ends are then tensioned to seat the device to the coracoid process 19, as shown in FIG. 20. A dimension of the eye 30 can be adjusted if desired, following the technique described above.

Wire loops or needles (not shown) on ends of pulling sutures 48'' and 50'' of the device 10'' are passed through a clavicular tunnel 62, to act as leaders. This is also shown in FIG. 20. It will be understood that two separate bone tunnels may be provided if required, as described elsewhere in this document.

Figure 21:
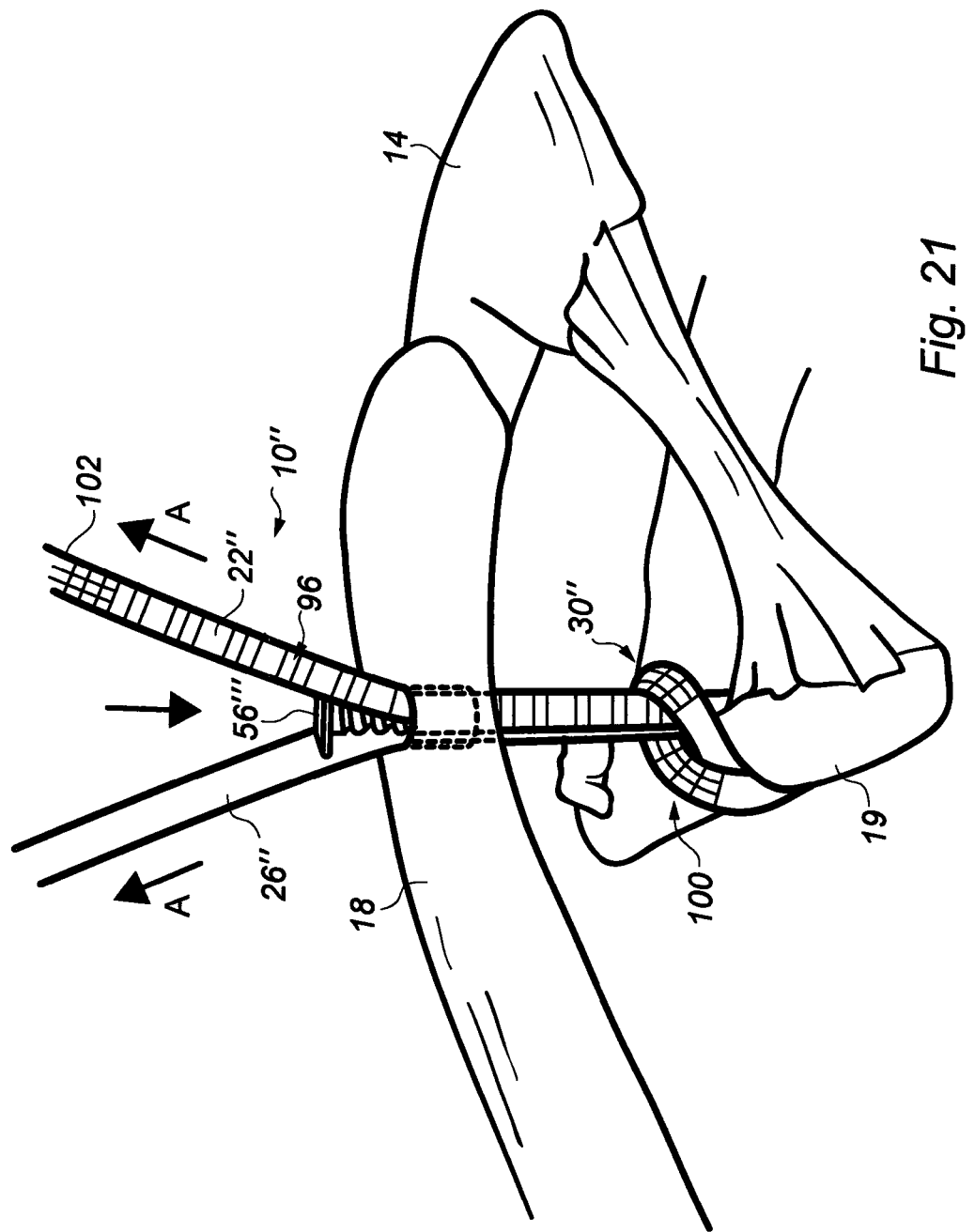

Each end of the joint stabilisation device 10'' is pulled to create tension, as shown by the arrows 'A' in FIG. 21, whilst holding the reduced ACJ. A bone reduction forceps (not shown) can again be used to assist with the reduction. Each end of the joint stabilisation device 10'' is then fixed in the clavicle tunnel 62 with a fixation device, in this case the screw 56''' of FIG. 15 (although any other device disclosed herein may be used).

Figure 22:
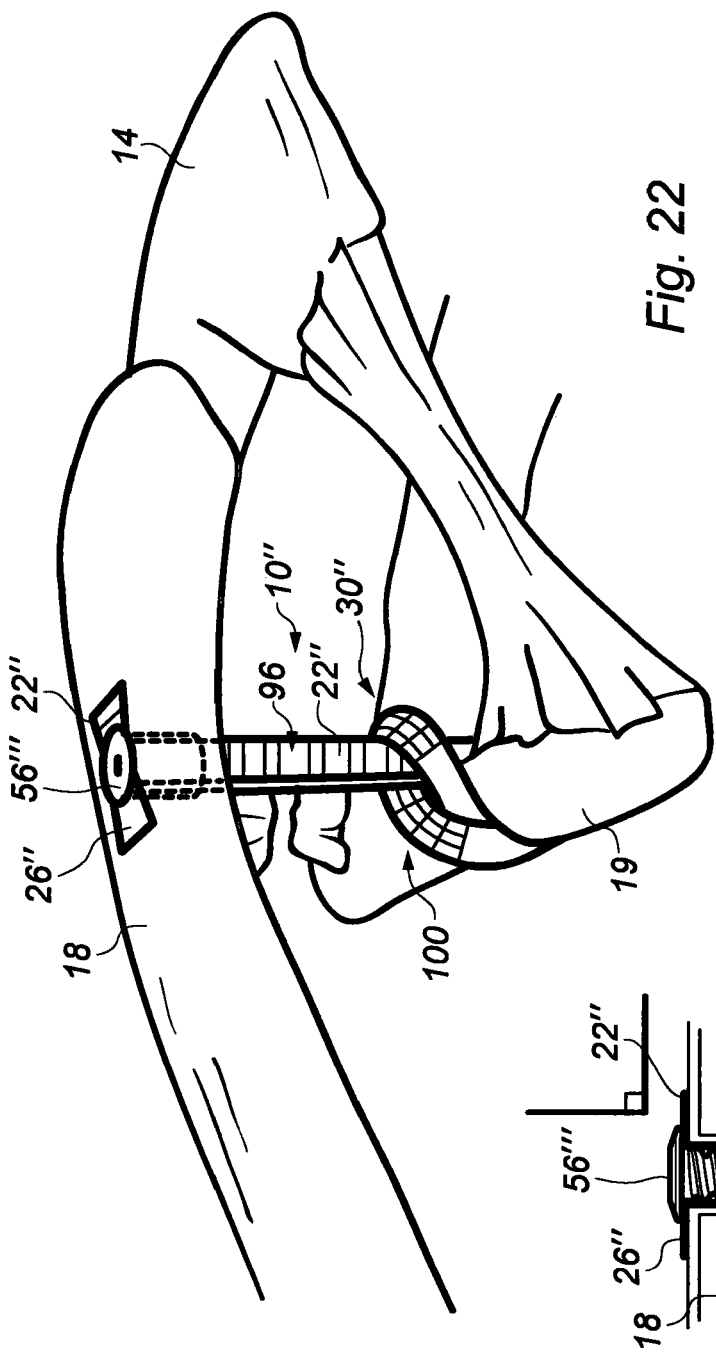
Figure 23:
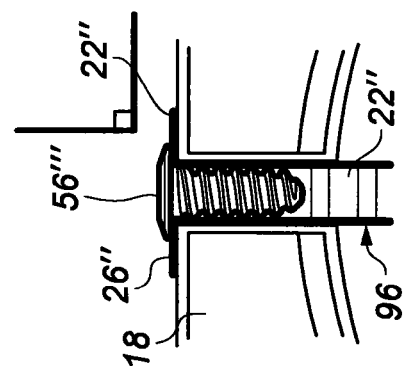

Remaining sections of the elongate portions 22'' and 26'' of the device 10'' (including the free ends 24'' and 28'') can then be severed as shown in FIG. 22. The arrangement of the screw 56''' and the stabilisation device 10'' is shown in the partial cross-sectional side view of FIG. 23. It will be understood that the indicators 96, 100 and 102 of the stabilisation device 10'' assist the surgeon at various stages in the procedure illustrated in FIGS. 18 to 23.

In one variation on this technique shown in FIG. 24, the elongate portions 22'' and 26'' are passed posteriorly around the clavicle 18, and the other anteriorly. The elongate portions 22'' and 26'' are then knotted underneath the clavicle 18, to form a knot 94''. This is essentially as shown in FIG. 11. Other variations on the technique employing the stabilisation device 10'' may follow any of the other methods disclosed herein.

As will be clear from the foregoing description, the assembly of the present invention can comprise a set of implants and a set of instruments to enable the repair of an ACJ. It may have the ability to be supplied in one size to fit all patients. The joint stabilisation device has an integral loop (eye) at one end, to allow it to be fixed to the coracoid process. The opposite end comprises two free ends of joint stabilisation device which will be passed through a bone tunnel or tunnels in the clavicle, and secured with a fixation device, which may be interference screw(s) or plugs(s), or an annular member. Alternatively it may be fixated by knotting the ends. Alternatively it may be fixated with a combination of a fixation device and a knot.

Any of above disclosed methods can be adapted for use in minimally invasive surgery with appropriate changes which will be readily appreciated by persons skilled in the art.

By supplying the fixation device(s) separate to the joint stabilisation device, a surgeon could purchase the number of fixation devices they require to do any technique disclosed herein. Alternatively the surgeon may only buy the joint stabilisation device and use a knotted fixation technique. A further fixation device could also be purchased if required to fixate the AC as well as CC repair devices. Thus the method/assembly of clavicular fixation is versatile, and creates potential for surgeons to develop new techniques in the future without the need for designing a new product. This also maintains excitement in the product and its market leader position during its lifecycle.

Various modifications may be made to the foregoing without departing from the spirit or scope of the present invention.

For example, the joint stabilisation device may comprise one or more tubular sections, a remainder or other parts of the device being non-tubular. At least a mid-section of the joint stabilisation device may be tubular, so that the eye can be formed at or in the mid-section.

The stabilisation device/assembly and method disclosed herein may have other uses than in the stabilisation of a dislocated ACJ. The stabilisation device may be used to perform at least part of the function of other damaged tissue, including but not restricted to tendons. For example, the stabilisation device/assembly and method may have a use in stabilisation of an elbow joint, and so of the collateral ligaments at the elbow, as well as repairs of distal biceps tendon avulsion.

The first and the second elongate portions may each comprise at least one indicator. In this situation, the at least one indicator associated with the first elongate portion may be a different indicator from the at least one indicator associated with the second elongate portion. The respective indicators of the elongate portions may have different characteristics, which may be visual characteristics. The at least one indicator of the first elongate portion may differ from the at least one indicator of the second elongate portion visually, and may for example be of different colours.

The invention claimed is:

1. A synthetic ligament or tendon for use as a joint stabilisation device, in which the synthetic ligament or tendon acts on behalf of a damaged ligament or tendon, comprising:
   a first elongate portion forming a first free end;
   a second elongate portion forming a second free end which is opposite the first free end; and an integral eye provided at a location which is between the first and second free ends, the eye serving for securing the device to a bone of a patient;

in which the device is at least partly tubular so as to define an internal cavity, said part of the device being of a woven material in which the woven material comprises warps extending in a direction parallel to a length of the device and wefts extending in a direction transverse to the warps;

and in which one of the first and second elongate portions extends into the internal cavity through a wall of the other one of the first and second elongate portions at a first location along a length of said other portion, and then extends out of the internal cavity at a second location which is spaced along a length of said other portion from the first location, to thereby form a loop which defines the eye.

2. A device as claimed in claim 1, in which a dimension of the loop is adjustable.

3. A device as claimed in claim 2, in which one of the first and second elongate portions is movable relative to the other one of the first and second elongate portions, to adjust a dimension of the loop.

4. A device as claimed in claim 3, in which the dimension of the loop is adjustable by sliding movement of said one of the elongate portions within the internal cavity relative said other one of the elongate portions.

5. A device as claimed in claim 1, in which a material forming the first and second elongate portions also forms the eye.

6. A device as claimed in claim 1, in which the eye comprises part of the first elongate portion and part of the second elongate portion.

7. A device as claimed in claim 1, in which the device is for stabilising an acromioclavicular joint (ACJ).

8. A device as claimed in claim 7, in which the joint stabilisation device is adapted to be secured to a coracoid process of the ACJ by passing the device around the coracoid process and directing the first and second free ends through the eye, to form a loop extending around the coracoid process;

and in which the joint stabilisation device is adapted to be secured to a clavicle of the ACJ.

9. A device as claimed in claim 1, comprising at least one indicator associated with a part of the device, the at least one indicator facilitating identification of said part of the device during use.

10. A device as claimed in claim 9, in which at least one of the first and second elongate portions comprises at least one indicator.

11. A device as claimed in claim 9, comprising a plurality of indicators, each indicator associated with a different part of the device.

12. A device as claimed in claim 9, in which the at least one indicator is a visual indicator having a visual characteristic.

13. A device as claimed in claim 9, comprising at least one first indicator having a first indicator characteristic, and at least one second indicator having a second indicator characteristic which is different from the first indicator characteristic.

14. A device as claimed in claim 9, comprising:
an indicator associated with the integral eye, facilitating identification of the eye; and
an indicator associated with at least one of the free ends, facilitating identification of said end.

15. A synthetic joint stabilisation assembly comprising:
a synthetic ligament or tendon for use as a joint stabilisation device according to claim 1; and
at least one fixation device, for securing at least one of the first and second elongate portions within a tunnel in a bone.

16. An assembly as claimed in claim 15, comprising:
a first fixation device adapted to be located in a first tunnel in the bone, and to engage the first elongate portion of the joint stabilisation device at a location which is spaced along a length of said portion from its free end; and
a second fixation device adapted to be located in a second tunnel in the bone, and
to engage the second elongate portion of the joint stabilisation device at a location which is spaced along a length of said portion from its free end.

17. An assembly as claimed in claim 15, in which the fixation device is adapted to be located in a tunnel in the bone, and to engage both the first and the second elongate portions of the joint stabilisation device at locations which are spaced along lengths of said portions from their free ends.

18. An assembly as claimed claim 15, in which the at least one fixation device comprises a locating part adapted to be located in the tunnel, and an abutment part adapted to abut an outer surface of the bone.

19. An assembly as claimed in claim 15, in which the at least one fixation device is a plug which is adapted to clamp at least one of the first and second elongate portions between an outer surface of the plug and a wall of the tunnel.

20. An assembly as claimed in claim 15, in which the at least one fixation device is a threaded device having an external thread which is adapted to engage a wall of the tunnel to secure the fixation device within the tunnel, and to clamp at least one of the first and second elongate portions between an outer surface of the fixation device and a wall of the tunnel.

21. An assembly as claimed in claim 15, in which the at least one fixation device comprises a passageway extending through the device, for receiving at least one of the first and second elongate portions.

22. An assembly as claimed in claim 20, in which the fixation device comprises a flange which is adapted to abut an outer surface of the bone to retain the device in the tunnel, wherein the flange defines an abutment surface for abutting an enlarged dimension section of at least one of the first and second elongate portions to secure the at least one elongate portion relative to the bone.

* * * * *